United States Patent
Ichim

(10) Patent No.: US 8,372,797 B2
(45) Date of Patent: Feb. 12, 2013

(54) TREATMENT OF ERECTILE DYSFUNCTION BY STEM CELL THERAPY

(75) Inventor: Thomas E. Ichim, San Diego, CA (US)

(73) Assignee: Creative Medical Health, Inc., Phoenix, AZ (US)

( * ) Notice: Subject to any disclaimer, the term of this patent is extended or adjusted under 35 U.S.C. 154(b) by 259 days.

(21) Appl. No.: 12/305,589

(22) PCT Filed: Jun. 22, 2007

(86) PCT No.: PCT/US2007/014525
§ 371 (c)(1),
(2), (4) Date: Aug. 24, 2009

(87) PCT Pub. No.: WO2007/149548
PCT Pub. Date: Dec. 27, 2007

(65) Prior Publication Data
US 2009/0311223 A1 Dec. 17, 2009

Related U.S. Application Data

(60) Provisional application No. 60/816,170, filed on Jun. 22, 2006.

(51) Int. Cl.
- A01N 61/00 (2006.01)
- A61K 31/00 (2006.01)
- C12N 5/00 (2006.01)
- C12N 5/08 (2006.01)

(52) U.S. Cl. .............. 514/1; 435/325; 435/372
(58) Field of Classification Search ...... 514/1; 435/325, 435/372
See application file for complete search history.

(56) References Cited

U.S. PATENT DOCUMENTS

| | | | |
|---|---|---|---|
| 5,916,569 A * | 6/1999 | Spencer et al. | 424/198.1 |
| 2003/0157071 A1* | 8/2003 | Wolfe et al. | |
| 2005/0084961 A1* | 4/2005 | Hedrick et al. | |
| 2006/0110825 A1* | 5/2006 | Alessandri et al. | |
| 2009/0104159 A1* | 4/2009 | Prosper et al. | |

OTHER PUBLICATIONS

Gonzalez-Cadavid et al., 2004, Endocrine, vol. 23, No. 2-3, p. 167-176.*
Caretta et al., 2005, Journal of Endocrinological Investigation, vol. 28, No. 11, Suppl Proceedings, Abstract only.*
Bochinski, et al., "The effect of neural embryonic stem cell therapy in a rat model of cavernosal nerve injury" *BJU International* (Oct. 2004) 94(6): 904-909.
Deng, et al., "Gene and stem cell therapy for erectile dysfunction" *International J. Impotence Research* (Dec. 2005) 17(1): S57-S63.
International Search Report issued in International Application No. PCT/US2007/014525, dated Nov. 6, 2008.

* cited by examiner

*Primary Examiner* — Shin-Lin Chen
(74) *Attorney, Agent, or Firm* — Baumgartner Patent Law; Marc Baumgartner

(57) ABSTRACT

Methods, cells and compositions of matter are provided for treatment of erectile dysfunction using stem cell therapy. In particular, various stem cells are modified or administered freshly isolated in order to induce smooth muscle regeneration, neural regeneration, and restoration of endothelial function. In some embodiments endogenous stem cells are mobilized or activated to achieve therapeutic benefit. In other embodiments compositions derived from stem cells are utilized for treatment of erectile dysfunction.

10 Claims, No Drawings

TREATMENT OF ERECTILE DYSFUNCTION BY STEM CELL THERAPY

CROSS-REFERENCE TO RELATED APPLICATIONS

This application claims priority under 35 U.S.C. §119 to U.S. Provisional Application Ser. No. 60/816,170, filed Jun. 22, 2006 which is incorporated herein by reference in its entirety.

BACKGROUND OF THE INVENTION

1. Field of the Invention

The invention pertains to the field of erectile dysfunction. More particularly it relates to cells useful for restoring erectile function including stem cells, regenerative cells, and angiogenesis promoting cells. More specifically, the invention relates to cord blood, bone marrow, peripheral blood, and specialized progenitor cells and products thereof.

2. Description of the Related Art

Erectile Dysfunction

Erectile dysfunction (ED) is characterized by the lack of ability to achieve and maintain penile erection for intercourse. The prevalence of ED is strongly correlated with increasing age. For example, according to the Massachusetts Male Aging Study, 67% of men 70 years of age experience some form of ED, whereas at age 40 only 39% of men report this [1]. ED is typically scored based on symptomology, although quantitative measurement instruments exist such as the Erectile Function Visual Analog Scale (EF-VAS) and the International Index of Erectile Function [2, 3]. An estimate of the number of Americans suffering from ED is believed to range from 10-30 million [4]. The prevalence of ED is illustrated by the fact that over 39 million prescriptions have been written for one ED drug, Viagra, in the United States as of 2006. World-wide it is believed that 100 million men are affected by various degrees of ED. Currently ED is treated by oral inhibitors of phosphodiesterase V, which is considered the standard of care. Despite this, numerous patients are unresponsive to treatment, do not tolerate adverse effects associated with treatment, or are ineligible for treatment. In order to properly overview the prior art relating to treatment of ED, and to provide a basis for the practitioner of the invention to utilize the invention disclosed optimally, it is necessary first to review the basic biology of the penis as relating to erections.

Penis Anatomy and Erection

The penis is comprised of three erectile bodies, 2 parallel ones termed corpora cavernosa, and underneath, wedged in between, the corpus spongiosum, which contains the urethra. The three erectile bodies are heavily vascularized and contain large proportion of smooth muscle cells. Erection is caused by neurologically-induced relaxation of smooth muscle cells in the erectile bodies, which allows influx and accumulation of blood into the balloon-like sacs between the smooth muscle cells called sinusoids. As blood accumulates, the outflow of blood is prevented by pressure from the tunica albuginea against the venous plexus, thus causing trapping of the blood, allowing erection to occur. The process of blood accumulation due to venous trapping is termed the veno-occlusive mechanism. Additional rigidity of the penis shaft is provided by contraction of the ischiocaverous muscles.

The initial nerve impulses triggering the erection originate from the brain in response to sexual stimuli. Although currently this area is under investigation, certain parts of the brain have been identified responsible for arousal. These include structures such as the frontal lobe, the hypothalamus, thalamus, amygdala and the cingulated gyrus [5]. The first identification of a brain structure associated with erection occurred in the 1960s in primate experiments using brain electrostimulation via a stereotactic technique. These studies demonstrated that stimulation of the medial frontal lobe led to erections in a consistently reproducible manner [6]. Subsequent clinical experiments demonstrated that during exposure to sexual stimuli, functional MRI could accurately identify increased perfusion activity in the frontal lobe, the cingulated gyrus, and the thalamus [7]. Interventional evidence of the importance of distinct anatomical areas in the central control of erection comes from clinical studies showing deep brain stimulation of the thalamic area for treatment of Tourette's syndrome leads to unexpected erections as a consequence [8]. Furthermore, the successful use of centrally acting drugs such as apomorphine in the treatment of ED, supports the importance of cerebral control of erection [9]. Older studies in pedophiles and rapists reported some success at the central inhibition of abnormal sex drive through the surgical ablation of certain anatomical regions of the hypothalamus [10].

In contrast to central regulation of erections, much more is known about spinal control. It is established that the sacral parasympathetic nucleus, the thoracolumbar sympathetic nuclei and the pudendal motoneurons are all involved in the stepwise transmission of signals between the dorsal penile nerves and central nervous system. Identification of specific areas was performed in studies, such as Stief et al, who showed that electrostimulation of the roots of S2 to S55 in man with complete thoracic spinal injury, was able to produce erection in all patients assessed [11]. A variety of electro-spinal stimulation of erection studies were reviewed by Giuliano et al [12]. From these studies it was identified that during normal erection, parasympathetic nervous activation causes relaxation of smooth muscle and dilation of the helicine arteries in the corpora cavernosum and the corpus spongiosum. This dilation, in combination with the veno-occlusive mechanism which prevents blood outflow from the penile body causes the end result of erection. Mechanistically, parasympathetic activation causes upregulation of nitric oxide (NO) production by nonadrenergic, noncholinergic nerves, as well as endothelium which lines the penile arteries and cavernosal sinusoids. Accumulation of NO increases production of cyclic guanosine monophosphate (cGMP) through activation of the enzyme guanylyl cyclase. cGMP acts as a second messenger which leads to decrease calcium uptake into the cavernous and endothelial-lining smooth muscles, thus causing relaxation and hence erection [13]. Since phosphodiesterase (PDE)-5 is involved in the breakdown of cGMP, the inhibition of PDE-5 has been chosen as a pharmacological goal of medications such as Viagra (sildenafil), Cialis (tadalafil) and Cialis (vardenafil) [14].

Causes of Erectile Dysfunction

It is known that ED is multifactorial, with causative influences including vasculogenic, endocrinological, psychogenic, and neurogenic. Some reports cite vascular disease as being culprit in as many as 85% of cases either directly or indirectly [15]. Accordingly this discussion begins with the endothelial cell dysfunction associated with ED. Vascular disease is associated with either decreased production of NO, or decreased responsiveness to its actions. There are 5 mechanisms postulated for decrease in this intermediate, all 5 associated with ED:

The first is oxidative stress in the form of the oxygen free radical superoxide, which both enhances degradation of NO (by direct conversion to peroxynitrite), as well as decreases its synthesis [16]. Importance of superoxide in induction of erectile dysfunction was demonstrated in experiments where administration of exogenous superoxide dismutase was able to increase erectile function in a model of rat diabetes associated ED [17].

The second mechanism is preformed advanced glycation end products, which are found in diabetics, as well as at higher concentrations in elderly patients [18]. These inactivate NO directly [19], induce an increased production of superoxide [20], which also inhibit NO as previously mentioned, and directly suppress synthesis of endothelial nitric oxide synthase (eNOS) by endothelial cells [21].

The third mechanism is enhanced expression of the enzyme arginase II [22], which compete with nitric oxide synthase for arginine. Thus enhanced arginase expression, which is associated with ED leads to inhibition of NO.

The forth mechanism is reduced transcription of eNOS and nNOS in tissue lacking testosterone [23, 24].

The fifth mechanism is increased activity of the Rho/Rho kinase which is associated with atherosclerosis. The Rho/Rho kinase both inhibits NOS activity and increases vascular smooth muscle tone, thereby inhibiting NO and erectile ability, respectively [25].

In all of the above five mechanisms, endothelial dysfunction seems to be the primary cause. Endothelial dysfunction is induced by aging, artherosclerotic changes, and oxidative stress. The essential role of the endothelium in ED is supported by studies, which demonstrate that ED onset is a precursor to other more serious cardiovascular diseases such as coronary heart disease before disease symptoms arise. For example in a study of 221 patients who were referred to undergo stress myocardial perfusion single-photon emission computed tomography (MPS), patients were screened for ED using a validated questionnaire. 54.8% of the screened patients demonstrated advanced ED. Patients with ED presented a higher level of coronary heart disease in comparison to patients without ED in terms of a summed MPS score>8, (43.0% vs 17.0%, respectively). ED patients also bad LVEF lower than 50% (24.0% vs 11.0%), shorter exercise time (8.0 vs 10.1 minutes) and lower Duke treadmill score (4.4 vs 8.4; P<0.001) in comparison to patients without ED. The role of ED as an independent predictor of severe coronary heart disease was identified using multivariate analysis (odds ratio, 2.50; 95% confidence interval, 1.24-5.04; P=0.01) [26]. In another study, 12 men with ED (IIEF-5 questionnaire score</=18) and 12 age-matched controls (IIEF-5 questionnaire score>/=21) were assessed for coronary flow velocity reserve by Doppler in the left anterior descending artery, before and during adenosine infusion. Flow velocity reserve was significantly reduced in subjects with erectile dysfunction: 2.36 versus 3.19; P=0.024. Using multivariate analysis, adjusting for age, tobacco use, systolic blood pressure, heart rate and body mass index, ED was the only significant predictor of reduced coronary flow velocity reserve, P=0.016 [27]. In another study, the severity of ED was compared with risk of heart disease. Men were stratified for risk for heart disease within 10 years using the Framingham risk profile algorithms. In the heart disease risk cohort men with moderate/severe ED (IIEF5 5-16) had a 65% increased relative risk for developing CHD within 10 yrs compared to those without ED (IIEF5 22-25). These data prompted the authors to state "Moderate to severe ED, but not mild ED is associated with a considerably increased risk for coronary heart disease" [28]. The possibility of ED being a predictive factor for development of more serious vascular diseases has prompted Montorsi et al to put forth the "Artery Size Hypothesis", in which the authors propose that smaller arteries, such as the pudendal arteries supplying blood to the penile structures, are more likely to be effected by artheroscierotic and other forms of endothelial damage, in comparison to larger vessels. Accordingly, the initiation of vascular disease is first identified in many cases as ED, which subsequently progresses to more advanced diseases. The authors make 4 points supporting this hypothesis, namely: a) ED and coronary artery disease should be considered as two different manifestations of the same disease process; b) Prevalence of occult coronary artery disease in ED should be low; c) Prevalence of ED in patients with coronary artery disease should be high; and d) Coronary artery disease should occur subsequently to ED in a wide variety of patients. The authors cite numerous supportive studies in a publications explaining their hypothesis [29].

The importance of the endothelial dysfunction in ED is exemplified by numerous assays, which have demonstrated not only correlation between dysfunction and ED, but also between reversion of ED and increased endothelial function. Studies demonstrating endothelial dysfunction include observations of reduced brachial flow dilation in ED patients [30, 31], reduced reactive hyperemic response [32], impaired mean blood pressure and platelet aggregation responses to L-arginine [33] and reduced endothelial precursor cells in circulation [34, 35]. Interventions that successful treat some forms of ED such as PDE5 inhibitors have been shown to increase both the numbers of circulating endothelial progenitors cells [36], as well as the brachial flow mediated dilation response [37-40]. Interestingly exercise [41], administration of statin drugs [42, 43], as well as pregnancy [44], has been demonstrated to correlate with increased numbers of circulating endothelial cells.

In animal models, administration of agents capable of inducing endothelial cell proliferation, and/or neoangiogenesis, induces inhibition of ED progression or reversion of ED. For example, basic fibroblast growth factor (bFGF) is a known inducer of angiogenesis in ischemic situations, and its exogenous administration is therapeutic in models of stroke [45], angina [46], and peripheral limb ischemia [47]. The administration of two 2.5 microgram doses of bFGF, separated by a 3-week interval into corporal tissue of hypercholesterolemic rabbits was shown to increase corporal relaxation in response to chemical stimuli, as well as ability to generate NO [48]. In another study, administration of bFGF intracavernously into diabetic rats by means of gelatin microbeads resulted in protection of erectile function from diabetes mediated onset [49]. Yet another study demonstrated that systemic basic fibroblast growth factor induces favorable histological changes in the corpus cavernosum of hypercholesterolemic rabbits [50].

Current Treatments of ED

The current standard of care for treatment of ED is phosphodiesterase inhibitors. For example, U.S. Pat. No. 5,250,534 discloses sildenafil (VIAGRA), an orally available PDE5 inhibitor. Additional PDE5 inhibitors include, Cialis (tadalafil) and Cialis (vardenafil). Unfortunately, a substantial number of patients (20-40%) are resistant to PDE5 inhibitors. These include substantial numbers of patients with advanced neurologic damage, diabetes mellitus, or vascular disease. This may be due to the fact that inhibition of PDE5 upregulates erectile mechanisms such as potentiating the effects of NO, but still depend on functional erectile tissue to be present in substantial concentrations. For example, a high adipose to smooth muscle ratio in cavernous tissue, as well as decreased expression or activity of neuronal or endothelial NO synthase (NOS), impaired NO release, accelerated NO destruction, and atrophy of cavernosal structures is associated with resistance of ED patients to PDE5 inhibitors [51, 52]. Accordingly, there is a need to develop means of regenerating erectile tissue, or components thereof in a natural and physiological manner as a means of treating ED instead of augmenting the activity of the already diminished tissue existing in patients with ED.

PDE5 inhibitors are known to possess a variety of systemic effects in numerous organ systems, therefore the long term effects of PDE5 inhibition are still uncertain. It is known that PDE5 inhibitors can induce a variety of adverse effects such as optic neuropathy [53], headaches [54], and various cardiovascular pathologies [55], especially when taken in combination with nitrates [56]. In fact, in 1998, the US Food and Drug Administration published a report on 130 confirmed deaths among men who received prescriptions for sildenafil citrate, with causes of death included arrythmias, sudden cardiac death and hypotension-associated events [57]. Beneficial non-ED uses of PDE5 inhibitors are known, for example, since PDE5 is expressed in lung tissue, investigators sought to, and succeeded at inhibiting symptomatic pulmonary arterial hypertension in a double blind clinical trial [58] by administration of sildenafil citrate. However, given the various areas in the body that PDE5 is expressed, such as platelets, kidneys, and pancreas [59], it is the belief of some that systemic inhibition of this enzymatic system may have physiologic consequences in the long-run [60].

Numerous other therapeutic products have been applied previously and some are still in use for treatment of ED. Non-pharmacological methods include the use of vacuum pumps, as well as penile prosthetic surgery. A penile prosthesis is described in U.S. Pat. No. 5,065,744.

Pharmacological methods include intracavernous administration of CAVERJECT (U.S. Pat. No. 4,127,118) and intraurethral administration of MUSE (U.S. Pat. No. 5,773,020) in which the active ingredient is PGE-1. Two serious adverse reactions associated with these agents are drug-induced pain and priapism. Specifically it is known that single use of PGE1 therapy produces a pain response in about 3 to 10 percent of patients, which increases with continued use. Additionally, manipulation of the penis prior to intercourse is not desirable by many patients. Treatments using intracavernosal injections are associated with a variety of adverse effects, which with increased occurrence have profound consequences. Said adverse effects include cutaneous ecchymosis, corporal fibrosis, and in some situations damage to the penile nerves. Pharmacological treatment methods that have been patented but have not been clinically approved include: a) U.S. Pat. No. 3,943,246, which describes treatment of impotence administration of oxytocin; U.S. Pat. No. 4,530,920 which describes nonapeptide and decapeptide analogs of luteinizing hormone releasing hormone agonists for treatment of ED; c) U.S. Pat. No. 4,139,617 which describes 19-oxygenated-androst-5-enes treatment of ED; and d) U.S. Pat. No. 5,541,211 which describes the use of yohimbine in treatment of ED.

Devices for intrascrotal implantation have been described in U.S. Pat. No. 5,518,499, which allow for administration of vasoactive agents such as PGE-1 without the need for intracavernousal injections. However this approach is highly invasive and does not treat the physiological cause of ED.

Centrally acting treatments for erectile dysfunction include apomorphine, as disclosed in U.S. Pat. No. 5,770,606. U.S. Pat. No. 4,801,587 discloses that phentolamine (VASOMAX®) which is available in a number of countries for treating hypertension is also useful for treating ED.

Details Regarding Diagnosis and Assessment of ED

This section will describe some of the details associated with diagnosis of ED. Although the invention describes numerous means of treatment of ED, it is important for the practitioner of the invention to realize the broad spectrum of diagnostic tools so that they will be able to decide which fit their respective patient populations.

ED is usually first assessed by the physical examination with special attention to possible penile and scrotal pathology or abnormalities, which may alter or inhibit the ability of the penis to cause penetration. Anatomical abnormalities or visible injuries are usually a small percentage of causative factors in ED. Subsequently, more detailed tests are performed such as the penobrachial blood pressure index (PBPI), doppler investigation of the penile arteries, and the papaverine test. These are described in detail in U.S. Pat. No. 6,132,757 and incorporated by reference herein. The PBPI is the penile systolic blood pressure divided by the systolic blood pressure determined at one of the arms. These blood pressures can be determined by any number of standard techniques. Thus, the penile systolic blood pressure can be determined by i) placing an inflatable cuff around the base of the free part of the penis in the flaccid state which is capable of being used to apply variable pressure, readable from a gauge, to an object around which the cuff is placed, ii) localizing the penile arteries with a Doppler ultrasound probe (e.g., 8 MHz probe, such as the Mini Doplex D500 available from Huntleigh Technology, Luton, United Kingdom), and then iii) inflating and deflating the cuff and ascertaining the pressure at which the Doppler sound reappears. The pressure at which the Doppler sound reappears is the penile systolic blood pressure. A male's penile blood pressure is regarded as normal if his PBPI is >0.80. With regard to Doppler investigation, each of the two penile cavernous arteries is investigated distal to the aforementioned cuff using the Doppler ultrasound problem. The function of each of the two arteries is assessed by Doppler ultrasound using an arbitrary scale of 0, 1, 2 or 3, where 0 means that the function is so deficient that the artery cannot be located and 3 means that the artery is well enough that maximal Doppler sound is observed. Detailed description of Doppler analysis and the papaverine tests are given in the following references [61-64]. The use of the Erectile Function Visual Analog Scale (EF-VAS) has become the golden standard for diagnosis and evaluation of treatment efficacy since it is based on overall functionality and not specific anatomical or biological abnormalities/defects.

SUMMARY OF THE INVENTION

Embodiments of the invention relate to methods of treating ED through the unified concept of stem cells possessing the dual ability of inhibiting progression of pathological processes associated with ED, as well as inducing regenerative activity capable of ameliorating and reversing said pathological processes.

In one aspect of the invention a patient with erectile dysfunction is administered one or several doses of CD34+ bone marrow derived stem cells at a concentration and/or frequency sufficient to induce endothelial responsiveness and nitric oxide production. Without being bound to any particular theory or mechanism, induction of endothelial cell responsiveness may be due to direct differentiation of said CD34+ cells into endothelial cells, or via production of factors. Administration of CD34+ cell dose and frequency can be based on a measurement of endothelial function, using assays such as the brachial flow mediated dilation assay. Through quantifying endothelial responsiveness to, and ability to produce, NO, said CD34+ cell infusion may be tailored in a patient-specific manner to allow restoration of erectile function. Monitoring of function can be performed based on symptomology, or on more quantitative scoring systems such as the Erectile Function Visual Analog Scale (EF-VAS) or the International Index of Erectile Function. Said CD34+ bone marrow cells may be either autologous, allogeneic, or xenogenic. In some variations, steps are taken to protect allogeneic or xenogenic cells from immune mediated rejection by the recipient. Said steps may include encapsulation, co-administration of an immune suppressive agent, or transfection of said cells with immune suppressory agent. In other variations, tolerance may be induced to said cells through immunological means. Said cells may be administered in combination with other agents known to increase erectile function, said agents include, but are not limited to inhibitors of PDE-5, PGE-1, papaverine, promorphine, or other known vasodilators.

In another aspect of the invention, stem cells are administered in combination with testosterone therapy. Said testosterone administration is provided at a concentration sufficient to induce smooth muscle cell growth in the areas associated with ED.

Thus, provided herein is a method of treating or preventing the onset of erectile dysfunction in a mammal comprising administering a therapeutically effective amount of cells capable of inducing one or more biological activities selected from the group that includes: a) inhibiting neuronal cell dysfunction, b) inhibiting cavernosal fibrosis, c) inhibiting smooth muscle degeneration, and d) inhibiting biological pathways causative of ischemia and the like.

Also provided is a method of treating or preventing the onset of erectile dysfunction in a mammal comprising administering a therapeutically effective amount of cells capable of inducing one or more biological activities selected from the group that includes: a) inducing regeneration of nervous tissue; b) stimulating smooth muscle cell activity; c) stimulating perfusion and the like.

Also provided is a method of treating or preventing the onset of erectile dysfunction in a mammal comprising administering a therapeutically effective amount of cells admixed with a factor.

Additionally, provided herein is the use of bone marrow stem cells, cord blood leukocytes, cord blood mesenchymal stem cells, cord blood mesenchymal stem cell supernatant concentrate, or adipose tissue-derived stem cell supernatant concentrate in the treatment of erectile dysfunction.

Further provided herein is the use of bone marrow stem cells, cord blood leukocytes, cord blood mesenchymal stem cells, cord blood mesenchymal stem cell supernatant concentrate, or adipose tissue-derived stem cell supernatant concentrate in the preparation of a medicament for the treatment of erectile dysfunction.

In certain aspects of the above embodiments, the erectile dysfunction can be caused in part by vascular insufficiency, neuronal dysfunction, or fibrosis of the corpora cavernous and/or the corpus spongiosum.

In certain aspects, the erectile dysfunction can be associated with injury. The injury can be, for example, traumatic, surgical, atherosclerotic, due to age associated degeneration, of structural elements, or of functional elements.

In certain aspects, the cells can be selected either alone or in combination from a group that includes: stem cells, committed progenitor cells, and differentiated cells. The stem cells can be selected from a group that includes: embryonic stem cells, cord blood stem cells, placental stem cells, bone marrow stem cells, amniotic fluid stem cells, neuronal stem cells, circulating peripheral blood stem cells, mesenchymal stem cells, germinal stem cells, adipose tissue derived stem cells, exfoliated teeth derived stem cells, hair follicle stem cells, dermal stem cells, parthenogenically derived stem cells, reprogrammed stem cells and side population stem cells and the like.

In certain aspects, the embryonic stem cells can be totipotent, and can express one or more antigens selected from a group that includes: stage-specific embryonic antigens (SSEA) 3, SSEA 4, Tra-1-60 and Tra-1-81, Oct-3/4, Cripto, gastrin-releasing peptide (GRP) receptor, podocalyxin-like protein (PODXL), Rex-1, GCTM-2, Nanog, and human telomerase reverse transcriptase (hTERT) and the like.

In certain aspects, the cord blood stem cells can be multipotent and capable of differentiating into endothelial, smooth muscle, and neuronal cells. The cord blood stem cells can be identified based on expression of one or more antigens selected from a group that includes: SSEA-3, SSEA-4, CD9, CD34, c-kit, OCT-4, Nanog, and CXCR-4 and the like. Further, the cord blood stem cells selected may not express one or more markers selected from a group that includes: CD3, CD34, CD45, and CD11b and the like.

In certain aspects, the placental stem cells can be isolated from the placental structure, and can be identified based on expression of one or more antigens selected from a group that includes: Oct-4, Rex-1, CD9, CD13, CD29, CD44, CD166, CD90, CD105, SH-3, SH-4, TRA-1-60, TRA-1-81, SSEA-4 and Sox-2 and the like.

In certain aspects, the bone marrow stem cells can be bone marrow mononuclear cells, and can be selected based on the ability to differentiate into one or more of the following cell types: endothelial cells, smooth muscle cells, and neuronal cells. The bone marrow stem cells can be selected based on expression of one or more of the following antigens: CD34, c-kit, flk-1, Stro-1, CD105, CD73, CD31, CD146, vascular endothelial-cadherin, CD133 and CXCR-4. Further, the bone marrow stem cells can be enriched for expression of CD133.

In certain aspects, the amniotic fluid stem cells can be isolated by introduction of a fluid extraction means into the amniotic cavity under ultrasound guidance. The amniotic fluid stem cells can be selected based on expression of one or more of the following antigens: SSEA3, SSEA4, Tra-1-60, Tra-1-81, Tra-2-54, HLA class I, CD13, CD44, CD49b, CD105, Oct-4, Rex-1, DAZL and Runx-1. Further, the amniotic fluid stem cells can be selected based on lack of expression of one or more of the following antigens: CD34, CD45, and HLA Class II.

In certain aspects, the neuronal stem cells can be selected based on expression of one or more of the following antigens: RC-2, 3CB2, BLB, Sox-2hh, GLAST, Pax 6, nestin, Muashi-1, NCAM, A2B5 and prominin.

In certain aspects, the circulating peripheral blood stem cells can be characterized by ability to proliferate in vitro for a period of over 3 months. Further, the circulating peripheral blood stem cells can be characterized by expression of CD34, CXCR4, CD117, CD113, and c-met. Further, the circulating peripheral blood stem cells may lack substantial expression of differentiation associated markers, such as, for example CD2, CD3, CD4, CD11, CD11a, Mac-1, CD14, CD16, CD19, CD24, CD33, CD36, CD38, CD45, CD56, CD64, CD68, CD86, CD66b, and HLA-DR and the like.

In certain aspects, the mesenchymal stem cells express one or more of the following markers: STRO-1, CD105, CD54, CD106, HLA-I markers, vimentin, ASMA, collagen-1, fibronectin, LFA-3, ICAM-1, PECAM-1, P-selectin, L-selectin, CD49b/CD29, CD49c/CD29, CD49d/CD29, CD61, CD18, CD29, thrombomodulin, telomerase, CD10, CD13, STRO-2, VCAM-1, CD146, and THY-1. Further, the mesenchymal stem cells may not express substantial levels of HLA-DR, CD117, and CD45. In certain aspects, the mesenchymal stem cells can be derived from a group selected of: bone marrow, adipose tissue, umbilical cord blood, placental tissue, peripheral blood mononuclear cells, differentiated embryonic stem cells, and differentiated progenitor cells.

In certain aspects, the germinal stem cells express markers selected from a group that includes: Oct4, Nanog, Dppa5 Rbm, cyclin A2, Tex18, Stra8, Daz1, beta1- and alpha6-integrins, Vasa, Fragilis, Nobox, c-Kit, Sca-1 and Rex1 and the like.

In certain aspects, the adipose tissue derived stem cells express markers selected from a group that includes: CD13, CD29, CD44, CD63, CD73, CD90, CD166, Aldehyde dehydrogenase (ALDH), and ABCG2 and the like. The adipose tissue derived stem cells can be a population of purified mononuclear cells extracted from adipose tissue capable of proliferating in culture for more than 1 month.

In certain aspects, the exfoliated teeth derived stem cells express markers selected from a group that includes: STRO-1, CD146 (MUC18), alkaline phosphatase, MEPE, and bFGF and the like.

In certain aspects, the hair follicle stem cells express markers selected from a group that includes: cytokeratin 15, Nanog, and Oct-4 and the like, and can be capable of proliferating in culture for a period of at least one month. The hair follicle stem cells may secrete one or more of the following proteins when grown in culture: basic fibroblast growth factor (bFGF), endothelin-1 (ET-1) and stem cell factor (SCF).

In certain aspects, the dermal stem cells express markers selected from a group that includes: CD44, CD13, CD29, CD90, and CD105 and the like, and can be capable of proliferating in culture for a period of at least one month.

In certain aspects, the parthenogenically derived stem cells can be generated by addition of a calcium flux inducing agent to activate an oocyte followed by enrichment of cells expressing markers selected from a group that includes SSEA-4, TRA 1-60 and TRA 1-81 and the like.

In certain aspects, the reprogrammed stem cells can be selected from a group that includes: cells subsequent to a nuclear transfer, cells subsequent to a cytoplasmic transfer, cells treated with a DNA methyltransferase inhibitor, cells treated with a histone deacetylase inhibitor, cells treated with a GSK-3 inhibitor, cells induced to dedifferentiate by alteration of extracellular conditions, and cells treated with various combination of the mentioned treatment conditions. In certain aspects, the nuclear transfer can include introducing nuclear material to a cell substantially enucleated, the nuclear material deriving from a host whose genetic profile is sought to be dedifferentiated. The cytoplasmic transfer can include introducing cytoplasm of a cell with a dedifferentiated phenotype into a cell with a differentiated phenotype, such that the cell with a differentiated phenotype substantially reverts to a dedifferentiated phenotype. The DNA demethylating agent can be selected from a group that includes: 5-azacytidine, psammaplin A, and zebularine and the like. The histone deacetylase inhibitor can be selected from a group that includes: valproic acid, trichostatin-A, trapoxin A and depsipeptide and the like.

In certain aspects, the side population cells can be identified based on expression multidrug resistance transport protein (ABCG2) or ability to efflux intracellular dyes such as rhodamine-123 and or Hoechst 33342. The side population cells can be derived from a tissue selected from the group that includes: pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue and the like.

In certain aspects, the committed progenitor cells can be selected from a group that includes: endothelial progenitor cells, neuronal progenitor cells, and hematopoietic progenitor cells and the like. Further, the committed endothelial progenitor cells can be purified from the bone marrow, or from peripheral blood, such as from peripheral blood of a patient whose committed endothelial progenitor cells can be mobilized by administration of a mobilizing agent or therapy. The mobilizing agent can be selected from a group that includes: G-CSF, M-CSF, GM-CSF, 5-FU, IL-1, IL-3, kit-L, VEGF, Flt-3 ligand, PDGF, EGF, FGF-1, FGF-2, TPO, IL-11, IGF-1, MGDF, NGF, HMG CoA-reductase inhibitors and small molecule antagonists of SDF-1 and the like. Further, the mobilization therapy can be selected from a group that includes: exercise, hyperbaric oxygen, autohemotherapy by ex vivo ozonation of peripheral blood, and induction of SDF-1 secretion in an anatomical can be outside of the bone marrow and the like.

In certain aspects, the committed endothelial progenitor cells express markers selected from a group that includes: CD31, CD34, AC133, CD146 and flk1 and the like.

In certain aspects, the committed hematopoietic cells can be purified from the bone marrow, or from peripheral blood, such as from peripheral blood of a patient whose committed hematopoietic progenitor cells can be mobilized by administration of a mobilizing agent or therapy. The mobilizing agent can be selected from a group that includes: G-CSF, M-CSF, GM-CSF, 5-FU, IL-1, IL-3, kit-L, VEGF, Flt-3 ligand, PDGF, EGF, FGF-1, FGF-2, TPO, IL-11, IGF-1, MGDF, NGF, HMG CoA-reductase inhibitors and small molecule antagonists of SDF-1 and the like. Further, the mobilization therapy can be selected from a group that includes: exercise, hyperbaric oxygen, autohemotherapy by ex vivo ozonation of peripheral blood, and induction of SDF-1 secretion in an anatomical can bea outside of the bone marrow.

In certain aspects, the committed hematopoietic progenitor cells can express the marker CD133 or CD34.

In certain aspects of the above embodiments, an antioxidant can be administered at a therapeutically sufficient concentration to a patient in need thereof. The antioxidant can be selected from a group that includes: ascorbic acid and derivatives thereof, alpha tocopherol and derivatives thereof, rutin, quercetin, hesperedin, lycopene, resveratrol, tetrahydrocurcumin, rosmarinic acid, Ellagic acid, chlorogenic acid, oleuropein, alpha-lipoic acid, glutathione, polyphenols, pycnogenol and the like. The antioxidant can be administered prior to administration of stem cells at a concentration sufficient to reduce oxidative stress from inhibiting the beneficial effects of the stem cells on erectile dysfunction. The antioxidant can be administered concurrently with stem cells in order to allow maximum stem cell beneficial function on erectile dysfunction. The antioxidant can be administered subsequent to stem cell administration in order to allow the administered stem cells to exert beneficial effects on erectile dysfunction.

In certain aspects of the above embodiments, an exercise regime can be provided to a patient suffering from erectile dysfunction, the exercise regime of sufficient duration to augment the beneficial effects of stem cells on erectile dysfunction.

In certain embodiments where a therapeutically effective amount of cells is admixed with a factor, the factor can have one or more of the following biological activities: induction of cell proliferation, inhibition of cell apoptosis, stimulation of angiogenesis, induction of cell de-differentiation, induction of cell regeneration. The factor can be selected from a group that includes: testosterone, a derivative or precursor thereof, thrombopoietin (TPO), stem cell factor (SCF), IL-1, IL-3, IL-7, flt-3 ligand (flt-31), a ligand of tie-2, G-CSF, GM-CSF, Epo, FGF-1, FGF-2, FGF-4, FGF-20, IGF, EGF, NGF, LIF, PDGF, bone morphogenic proteins (BMP), activin-A, VEGF, forskolin, and glucocorticords and the like. In certain aspects, a therapeutic amount of testosterone can be applied systemically. The factor can be a DNA demethylating agent such as 5-azacytidine, psammaplin A, and zebularine. The factor can be a histone deacetylase inhibitor such as valproic acid, trichostatin-A, trapoxin A and depsipeptide.

Also provided herein is a method of treating or preventing the onset of erectile dysfunction in a mammal, comprising administering a therapeutically effective amount of a factor capable of inducing endogenous stem cell mobilization. In certain aspects, the endogenous stem cells can be capable of enhancing cavernous smooth muscle content relative to connective and/or adipose tissue content. The factor capable of inducing endogenous stem cell mobilization can be selected from a group that includes: a CXCR-4 antagonist, AMD3100, G-CSF, M-CSF, GM-CSF, IL-1, IL-3, IL-8, G-CSF, a statin, and a chemotherapeutic drug. In certain aspects, a chemoattractant can be provided at a concentration sufficient to increase homing of endogenous stem cells into an can bea of need, such that increased stem cell migration contributes to prevention or reversion of erectile dysfunction. The chemoattractant can be selected from a group that includes: SDF-1, VEGF, various isoforms thereof and small molecule agonists of VEGFR-1, VEGFR2, and CXCR4. The chemoattractant can be localized by means of intracavernousal injection, or by means of administration in an agent capable of substantially localizing the chemoattractant. The agent capable of substantially localizing the chemoattractant can be selected from a group that includes: fibrin glue, polymers of polyvinyl chloride, polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, polyethylene oxide, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl flouride, polyvinyl imidazole, chlorosulphonated polyolifins, and polyvinyl alcohol.

In certain aspects, an agent can be administered that is capable of stimulating proliferation of endogenous stem cells. The agent capable of stimulating proliferation of endogenous stem stems can be selected from a group that includes: prolactin, HCG, testosterone and LH, and the like.

Also provided is a method of treating erectile dysfunction comprising administering a therapeutically sufficient concentration of products produced by stem cells.

The products can be administered systemically or locally, and can be administered in combination with exogenous stem cells, or in combination with mobilized endogenous stem cells. The products can be supernatants of stem cells, and the supernatants can be collected after culture of stem cells under substantially physiological conditions, or after culture of stem cells under substantially unphysiological conditions. The supernatants can be collected after culture of stem cells in conditions that stimulate secretion of angiogenic factors. The conditions stimulating secretion of angiogenic factors can be selected from a group that includes hypoxia, inducers of HIF-1 expression in the cells, inducers of VEGF in the cells, and inducers of FGF-1 in the cells and the like. In certain aspects, the condition stimulating secretion of angiogenic factors can be hypoxia.

In certain aspects, the product produced by stem cells can be concentrated in a physiological solution before administration. In certain aspects, the product produced by stem cells can be induced by treatment of the stem cells with an inducing agent. The inducing agent can, for example, endow the stem cells ability to increase production of factors therapeutically useful for treatment of erectile dysfunction. The inducing agent can be selected from a group that includes: one or more growth factors, one or more dedifferentiating factors, and one or more survival promoting factors and the like. The growth factors can be selected from a group that includes: vascular endothelial growth factor, hepatocyte growth factor, adrenomedullin, nerve growth factor, brain derived neurotrophic factor, testosterone, and insulin-like growth factor-1 and the like. The dedifferentiating factors can be selected from a group that includes: a DNA methyltransferase inhibitor, a histone deacetylase inhibitor, and cytoplasm of a substantially less differentiated cell in respect to the stem cell chosen for production of cellular product for treatment of erectile dysfunction and the like. The survival factor can be selected from a group that includes: FGF-1, FGF-2, FGF-4, bcl-2, and bcl-X1 and the like.

In certain aspects, the cells can be selected either alone or in combination from a group that includes: stem cells, committed progenitor cells, and differentiated cells. The stem cells can be selected from a group that includes: embryonic stem cells, cord blood stem cells, placental stem cells, bone marrow stem cells, amniotic fluid stem cells, neuronal stem cells, circulating peripheral blood stem cells, mesenchymal stem cells, germinal stem cells, adipose tissue derived stem cells, exfoliated teeth derived stem cells, hair follicle stem cells, dermal stem cells, parthenogenically derived stem cells, reprogrammed stem cells and side population stem cells and the like.

In certain aspects, the embryonic stem cells can be totipotent, and can express one or more antigens selected from a group that includes: stage-specific embryonic antigens (SSEA) 3, SSEA 4, Tra-1-60 and Tra-1-81, Oct-3/4, Cripto, gastrin-releasing peptide (GRP) receptor, podocalyxin-like protein (PODXL), Rex-1, GCTM-2, Nanog, and human telomerase reverse transcriptase (HTERT) and the like.

In certain aspects, the cord blood stem cells can be multipotent and capable of differentiating into endothelial, smooth muscle, and neuronal cells. The cord blood stem cells can be identified based on expression of one or more antigens selected from a group that includes: SSEA-3, SSEA-4, CD9, CD34, c-kit, OCT-4, Nanog, and CXCR-4 and the like. Further, the cord blood stem cells selected may not express one or more markers selected from a group that includes: CD3, CD34, CD45, and CD11b and the like.

In certain aspects, the placental stem cells can be isolated from the placental structure, and can be identified based on expression of one or more antigens selected from a group that includes: Oct-4, Rex-1, CD9, CD13, CD29, CD44, CD166, CD90, CD105, SH-3, SH-4, TRA-1-60, TRA-1-81, SSEA-4 and Sox-2 and the like.

In certain aspects, the bone marrow stem cells can be bone marrow mononuclear cells, and can be selected based on the ability to differentiate into one or more of the following cell types: endothelial cells, smooth muscle cells, and neuronal cells. The bone marrow stem cells can be selected based on expression of one or more of the following antigens: CD34, c-kit, flk-1, Stro-1, CD105, CD73, CD31, CD146, vascular endothelial-cadherin, CD133 and CXCR-4. Further, the bone marrow stem cells can be enriched for expression of CD133.

In certain aspects, the amniotic fluid stem cells can be isolated by introduction of a fluid extraction means into the amniotic cavity under ultrasound guidance. The amniotic fluid stem cells can be selected based on expression of one or more of the following antigens: SSEA3, SSEA4, Tra-1-60, Tra-1-81, Tra-2-54, HLA class I, CD13, CD44, CD49b, CD105, Oct-4, Rex-1, DAZL and Runx-1. Further, the amniotic fluid stem cells can be selected based on lack of expression of one or more of the following antigens: CD34, CD45, and HLA Class II.

In certain aspects, the neuronal stem cells can be selected based on expression of one or more of the following antigens: RC-2, 3CB2, BLB, Sox-2hh, GLAST, Pax 6, nestin, Muashi-1, NCAM, A2B5 and prominin.

In certain aspects, the circulating peripheral blood stem cells can be characterized by ability to proliferate in vitro for a period of over 3 months. Further, the circulating peripheral blood stem cells can be characterized by expression of CD34, CXCR4, CD117, CD113, and c-met. Further, the circulating peripheral blood stem cells may lack substantial expression of differentiation associated markers, such as, for example CD2, CD3, CD4, CD11, CD11a, Mac-1, CD14, CD16, CD19, CD24, CD33, CD36, CD38, CD45, CD56, CD64, CD68, CD86, CD66b, and HLA-DR and the like.

In certain aspects, the mesenchymal stem cells express one or more of the following markers: STRO-1, CD105, CD54, CD106, HLA-I markers, vimentin, ASMA, collagen-1, fibronectin, LFA-3, ICAM-1, PECAM-1, P-selectin, L-selectin, CD49b/CD29, CD49c/CD29, CD49d/CD29, CD61, CD18, CD29, thrombomodulin, telomerase, CD10, CD13, STRO-2, VCAM-1, CD146, and THY-1. Further, the mesenchymal stem cells may not express substantial levels of HLA-DR, CD117, and CD45. In certain aspects, the mesenchymal stem cells can be derived from a group selected of: bone marrow, adipose tissue, umbilical cord blood, placental tissue, peripheral blood mononuclear cells, differentiated embryonic stem cells, and differentiated progenitor cells.

In certain aspects, the germinal stem cells express markers selected from a group that includes: Oct4, Nanog, Dppa5 Rbm, cyclin A2, Tex18, Stra8, Daz1, beta1- and alpha6-integrins, Vasa, Fragilis, Nobox, c-Kit, Sca-1 and Rex1 and the like.

In certain aspects, the adipose tissue derived stem cells express markers selected from a group that includes: CD13, CD29, CD44, CD63, CD73, CD90, CD166, Aldehyde dehydrogenase (ALDH), and ABCG2 and the like. The adipose tissue derived stem cells can be a population of purified mononuclear cells extracted from adipose tissue capable of proliferating in culture for more than 1 month.

In certain aspects, the exfoliated teeth derived stem cells express markers selected from a group that includes: STRO-1, CD146 (MUC18), alkaline phosphatase, MEPE, and bFGF and the like.

In certain aspects, the hair follicle stem cells express markers selected from a group that includes: cytokeratin 15, Nanog, and Oct-4 and the like, and can be capable of proliferating in culture for a period of at least one month. The hair follicle stem cells may secrete one or more of the following proteins when grown in culture: basic fibroblast growth factor (bFGF), endothelin-1 (ET-1) and stem cell factor (SCF).

In certain aspects, the dermal stem cells express markers selected from a group that includes: CD44, CD13, CD29, CD90, and CD105 and the like, and can be capable of proliferating in culture for a period of at least one month.

In certain aspects, the parthenogenically derived stem cells can be generated by addition of a calcium flux inducing agent to activate an oocyte followed by enrichment of cells expressing markers selected from a group that includes SSEA-4, TRA 1-60 and TRA 1-81 and the like.

In certain aspects, the reprogrammed stem cells can be selected from a group that includes: cells subsequent to a nuclear transfer, cells subsequent to a cytoplasmic transfer, cells treated with a DNA methyltransferase inhibitor, cells treated with a histone deacetylase inhibitor, cells treated with a GSK-3 inhibitor, cells induced to dedifferentiate by alteration of extracellular conditions, and cells treated with various combination of the mentioned treatment conditions. In certain aspects, the nuclear transfer can include introducing nuclear material to a cell substantially enucleated, the nuclear material deriving from a host whose genetic profile is sought to be dedifferentiated. The cytoplasmic transfer can include introducing cytoplasm of a cell with a dedifferentiated phenotype into a cell with a differentiated phenotype, such that the cell with a differentiated phenotype substantially reverts to a dedifferentiated phenotype. The DNA demethylating agent can be selected from a group that includes: 5-azacytidine, psammaplin A, and zebularine and the like. The histone deacetylase inhibitor can be selected from a group that includes: valproic acid, trichostatin-A, trapoxin A and depsipeptide and the like.

In certain aspects, the side population cells can be identified based on expression multidrug resistance transport protein (ABCG2) or ability to efflux intracellular dyes such as rhodamine-123 and or Hoechst 33342. The side population cells can be derived from a tissue selected from the group that includes: pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue and the like.

In some embodiments, the therapeutic product produced by stem cells is administered locally into a patient in need thereof in combination with a delivery agent, the delivery agent selected from a group that includes: fibrin glue, polymers of polyvinyl chloride, polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, polyethylene oxide, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl flouride, polyvinyl imidazole, chlorosulphonated polyolifins, and polyvinyl alcohol and the like.

Also provided herein is method of treating erectile dysfunction by administration of a therapeutically sufficient amount of testosterone in combination with stem cells.

Also provided herein is a method of prophylactically treating coronary artery disease through intervening at the stage of erectile dysfunction onset.

DETAILED DESCRIPTION OF THE PREFERRED EMBODIMENT

Embodiments of the invention relate to novel methods of reversing or substantially ameliorating the processes associated with erectile dysfunction through the therapeutic administration of cells, which are either stem cells, progenitor cells, or differentiated cells, products generated from said cells, or combinations of cells, products, and currently used therapeutics.

Accordingly, provided herein are methods and compositions for treating or preventing the onset of erectile dysfunction in a mammal. In one embodiment, a therapeutically effective amount of cells are administered that are capable of inhibiting neuronal cell dysfunction, inhibiting cavernosal fibrosis, inhibiting smooth muscle degeneration or inhibiting biological pathways causative of ischemia. In another embodiment, a therapeutically effective amount of cells are administered that are capable of inducing regeneration of nervous tissue, stimulating smooth muscle cell activity, or stimulating perfusion. In another embodiment, a therapeutically effective amount of cells is admixed with a factor. In another embodiment, a therapeutically sufficient concentration of products produced by stem cells is administered. In some embodiments, a therapeutically sufficient amount of testosterone is administered in combination with stem cells.

As used herein, a therapeutically effective amount, therapeutically sufficient amount, therapeutically effective concentration and like terms refer to an amount of an agent sufficient to ameliorate at least one symptom, behavior or event, associated with a pathological, abnormal or otherwise undesirable condition, e.g., erectile dysfunction, or an amount sufficient to prevent or lessen the probability that such a condition will occur or re-occur, or an amount sufficient to delay worsening of such a condition. In one embodiment, the term therapeutically effective amount and like terms are used to refer to an amount having the effect of treating or preventing the onset of erectile dysfunction in a mammal.

Autologous Stem Cells for ED Therapy

The underlying theme of the invention teaches the use of cells with stem cell-like properties for the treatment of erectile dysfunction. Specific properties of stem cells that are suitable for use in practicing the current invention are: a) ability to both increase endothelial function, as well as induce neoangiogenesis; b) ability to prevent atrophy, as well as to differentiate into functional penile tissue; and c) ability to induce local resident stem/progenitor cells to proliferate through secretion of soluble factors, as well as via membrane bound activities. In one embodiment of the invention, stem cells are collected from an autologous patient, expanded ex vivo, and reintroduced into said patient at a concentration and frequency sufficient to cause therapeutic benefit in ED. Said stem cells are selected for ability to cause: neoangiogenesis, prevention of tissue atrophy, and regeneration of functional tissue. Stem cells chosen may be selected from a group consisting of: embryonic stem cells, cord blood stem cells, placental stem cells, bone marrow stem cells, amniotic fluid stem cells, neuronal stem cells, circulating peripheral blood stem cells, mesenchymal stem cells, germinal stem cells, adipose tissue derived stem cells, exfoliated teeth derived stem cells, hair follicle stem cells, dermal stem cells, parthenogenically derived stem cells, reprogrammed stem cells and side population stem cells.

Selection of Stem Cells for ED Therapy

When selecting stem cells for use in the practice of the current invention, several factors must be taken into consideration, such as: ability for ex vivo expansion without loss of therapeutic activity, ease of extraction, general potency of activity, and potential for adverse effects. Ex vivo expansion ability of stem cells can be measured using typical proliferation and colony assays known to one skilled in the art, while identification of therapeutic activity depends on functional assays that test biological activities such as: ability to support endothelial function, ability to protect neurons from degeneration/atrophy, and, ability to inhibit smooth muscle atrophy/degeneration. Assessment of therapeutic activity can also be performed using surrogate assays which detect markers associated with a specific therapeutic activity. Such markers include CD34 or CD133, which are associated with stem cell activity and ability to support angiogenesis [65]. Other assays useful for identifying therapeutic activity of stem cell populations for use with the current invention include evaluation of production of factors associated with the therapeutic activity desired. For example, identification and quantification of production of FGF, VEGF, angiopoietin, or other such angiogenic molecules may be used to serve as a guide for approximating therapeutic activity in vivo [66]. Additionally, secretion of factors that inhibit smooth muscle atrophy or neuronal dysfunction may also be used as a marker for identification of cells that are useful for practicing the current invention.

Embryonic Stem Cells

For use in the context of the present invention, embryonic stem cells possess certain desirable properties, such as the ability to differentiate to almost every cell comprising the host. Additionally, embryonic stem cells secrete numerous factors capable of inhibiting the process of ED. Unfortunately, certain drawbacks exist that limit the utility of this cell type for widespread therapeutic implementation. The potential for carcinogenicity is apparent in that human embryonic stem cells administered to immunocompromised mice leads to formation of teratomas [67]. Accordingly, for use in the current invention, embryonic stem cells have to be either differentiated into a stem cell, or a progenitor cell that is not capable of forming tumors. Cells useful the practice of the current invention should not differentiate in a substantial amount in an uncontrolled manner or into tissue which is pathological to the patient's well being. Although several technologies are currently being tested for selecting embryonic stem cells that do not cause teratomas, these methods are still in their infancy [68]. Therefore, one method of utilizing embryonic stem cells for the practice of this invention is to encapsulate said embryonic stem cells, or place said cells into a permeable barrier so as to allow for secretion of therapeutic factors elaborated by said cells without the risk of causing cancer or undesired tissue growth. The use of said encapsulation technology has been successful in "semi-isolating" cells with therapeutic potential from the body, for examples of this the practitioner of the invention is referred to work on microencapsulation of islets for treatment of diabetes, in which cases xenogeneic islets are used [69, 70], or other systems of therapeutic cellular xenograft therapy [71-73]. Said encapsulated cells may be administered systemically, or in a preferred embodiment locally in an area proximal to penile circulation, such as the fat tissue adjacent to the pudendal artery. Alternatively, encapsulated cells may be placed in a removable chamber in subcutaneous tissue similarly to the one described in U.S. Pat. No. 5,958,404. The advantages of using a removable chamber is that administration of cell therapy is not a permanent intervention and may be withdrawn upon achievement of desired therapeutic effect, or at onset of adverse effects.

Another embodiment of the current invention is the use of embryonic stem cell supernatant as a therapy for ED. Specific embodiments include identification of substantially purified fractions of said supernatant capable of inducing endothelial cell proliferation, smooth muscle regeneration, and/or neuronal cell proliferation/survival. Identification of such therapeutically active fractions may be performed using methods commonly known to one skilled in the art, and includes separation by molecular weight, charge, affinity towards substrates and other physico-chemical properties. In one particular embodiment, supernatant of embryonic stem cell cultures is harvested substantially free from cellular contamination by use of centrifugation or filtration. Supernatant may be concentrated using means known in the art such as solid phase extraction using C18 cartridges (Mini-Speed C18-14%, S.P.E. Limited, Concord ON). Said cartridges are prepared by washing with methanol followed by deionized-distilled water. Up to 100 ml of embryonic stem cell supernatant may be passed through each cartridge before elution. After washing the cartridges material adsorbed is eluted with 3 ml methanol, evaporated under a stream of nitrogen, redissolved in a small volume of methanol, and stored at 4.degree. C. Before testing the eluate for activity in vitro, the methanol is evaporated under nitrogen and replaced by culture medium. Said C18 cartridges are used to adsorb small hydrophobic molecules from the embryonic stem cell culture supernatant, and allows for the elimination of salts and other polar contaminants. It may, however be desired to use other adsorption means in order to purify certain compounds from the embryonic stem cell supernatant. Said concentrated supernatant may be assessed directly for biological activities useful for the practice of this invention, or may be further purified. Further purification may be performed using, for example, gel filtration using a Bio-Gel P-2 column with a nominal exclusion limit of 1800 Da (Bio-Rad, Richmond Calif.). Said column may be washed and pre-swelled in 20 mM Tris-HCl buffer, pH 7.2 (Sigma) and degassed by gentle swirling under vacuum. Bio-Gel P-2 material be packed into a 1.5.times.54 cm glass column and equilibrated with 3 column volumes of the same buffer. Embryonic stem cell supernatant concentrates extracted by C18 cartridge may be dissolved in 0.5 ml of 20 mM Tris buffer, pH 7.2 and run through the column. Fractions may be collected from the column and analyzed for biological activity. Other purification, fractionation, and identification means are known to one skilled in the art and include anionic exchange chromatography, gas chromatography, high performance liquid chromatography, nuclear magnetic resonance, and mass spectrometry. Administration of supernatant active fractions may be performed locally or systemically.

For the practice of the invention, the practitioner is referred to the numerous methods of generating embryonic stem cells that are known in the art. Patents describing the generation of embryonic stem cells include U.S. Pat. No. 6,506,574 to Rambhatla, U.S. Pat. No. 6,200,806 to Thomson, U.S. Pat. No. 6,432,711 to Dinsmore, and U.S. Pat. No. 5,670,372 to Hogan, each of which is incorporated by reference herein in its entirety. In one embodiment of the invention, embryonic stem cells are differentiated into endothelial progenitor cells in vitro, followed by administration to a patient in need of therapy at a concentration and frequency sufficient to ameliorate or cure ED. Differentiation into endothelial progenitors may be performed by several means known in the art [74]. One such means includes generation of embryoid bodies through growing human embryonic stem cells in a suspension culture. Said embryoid bodies are subsequently dissociated and cells expressing endothelial progenitor markers are purified [75]. Purification of endothelial cells from embryoid bodies can be performed using, of example, selection for PECAM-1 expressing cells. Purified cells can be expanded in culture and used for injection. Another alternative method of generating endothelial progenitors from embryonic stem cells involves removing media from embryonic stem cells a period of time after said embryonic stem cells are plated and replacing said media with a media containing endothelial-differentiating factors. For example, after plating of embryonic stem cells for a period between 6 and 48 hours, but more preferably between 20 and 24 hours, the original media in which embryonic stem cells were cultured is washed off the cells and endothelial cell basal medium-2 (EBM2), with 5% fetal calf serum, VEGF, bFGF, IGF-1, EGF, and ascorbic acid is added to the cells. This combination is commercially available (EGM2-MV Bullet Kit; Clonetics/BioWhittaker, Walkersville, Md.). By culturing the embryonic stem cells for 20-30 days in the EGM2 medium, with changing of media every 3 to 5 days, a population of endothelial progenitors can be obtained. For such cells to be useful in the practice of the present invention, functionality of said endothelial precursors, and their differentiated progeny must be assessed. Methods of assessing endothelial function include testing their ability to produce and respond to NO, as well as ability to form cord-like structures in Matrigel, and/or form blood vessels when injected into immunocompromised mice [76]. Endothelial cells, or endothelial precursor cells, generated from embryonic stem cells may be administered to the patient in an injection solution, which may be saline, mixtures of autologous plasma together with saline, or various concentrations of albumin with saline. Ideally pH of the injection solution is from about 6.4 to about 8.3, optimally 7.4. Excipients may be used to bring the solution to isotonicity such as, 4.5% mannitol or 0.9% sodium chloride, pH buffers with art-known buffer solutions, such as sodium phosphate. Other pharmaceutically acceptable agents can also be used to bring the solution to isotonicity, including, but not limited to, dextrose, boric acid, sodium tartrate, propylene glycol, polyols (such as mannitol and sorbitol) or other inorganic or organic solutes. Injection can be performed systemically, with the goal of injected cells homing to penile tissues associated with ED, or alternatively administration may be local, via intracavernosal administration. In variations of the invention where endothelial progenitors/endothelial cells are administered systemically, the local administration of an endothelial progenitor/endothelial cell chemoattractant factor may be used in order to increase the number of cells homing to the area of need. Said chemoattractant factors may include SDF-1 and/or VEGF, various isoforms thereof and small molecule agonists of the VEGFR-1 and/or VEGFR2, and/or CXCR4. Localization of said chemotactic factors to the area causative of ED may be performed using agents such as fibrin glue or certain delivery polymers known to one who is skilled in the art, these may include: polyvinyl chloride, polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, polyethylene oxide, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl flouride, polyvinyl imidazole, chlorosulphonated polyolifins, and polyvinyl alcohol. Acceptable carriers, excipients, or stabilizers are also contemplated within the current invention, said carriers, excipients and stabilizers being relatively nontoxic to recipients at the dosages and concentrations employed, and may include buffers such as phosphate, citrate, and other organic acids; antioxidants including ascorbic acid, n-acetylcysteine, alpha tocopherol, and methionine; preservatives such as hexamethonium chloride; octadecyldimethylbenzyl ammonium chloride; benzalkonium chloride; phenol, benzyl alcohol, or butyl; alkyl parabens such as methyl or propyl paraben; catechol; resorcinol; cyclohexinol; 3-pentanol; and me-cresol); low molecular weight polypeptides; proteins, such as gelatin, or non-specific immunoglobulins; amino acids such as glycine, glutamine, asparagine, histidine, arginine, or lysine; monosaccharides, disaccharides, and other carbohydrates including glucose, mannose, or dextrins; chelating agents such as. EDTA; sugars such as sucrose, mannitol, trehalose, or sorbitol; salt-forming counter-ions such as sodium; metal complexes. Chemoattraction of cells with stem cell-like properties has been described in US Patent Application No 2006/0003312 to Blau, which is incorporated by reference herein in its entirety.

In another embodiment, embryonic stem cells are induced to differentiate into the neuronal lineage in vitro, prior to administration into a patient suffering from ED. Said differentiation may be performed by alteration of culture conditions, such as growing embryonic stem cells in suspension culture so as to allow formation of embryoid bodies, and collecting the neuronally differentiated cells from said embryoid bodies, followed by in vitro expansion. Collection of the neuronally differentiated cells may be performed through selective isolation of cells expressing markers associated with the neuronal lineage, said markers include, but are not limited to: polysialyated N-CAM, N-CAM, A2B5, nestin and vimentin. Alternatively, embryonic stem cells may be induced to differentiate into the neuronal lineage through culture in factors that stimulate such differentiation. Said factors include NGF, neurotropnin-3 and retinoic acid may be added to cultures to support differentiation [77]. Cells may be cultured in suspension, or as adherent cultures, or using scaffolds fabricated from materials known to be biodegradable such as poly-alpha-hydroxy esters, for example poly-lactic-co-glycolic acid and poly-L-lactic acid [75]. Assessment of maturity of cultured neuronal cells can be performed using markers such as glutamate, synaptophysin, glutamic acid decarboxylase, serotonin, tyrosine hydroxylase, and GABA. Said neuronal cells may be administered systemically, or locally in a patient with ED. Administration of cells may be performed as described above in terms of formulations and co-factors to promote migration to area of need.

In another embodiment, embryonic stem cells are induced to differentiate into the smooth muscle lineage. The invention may be practiced by administration of either smooth muscle progenitor cells, or differentiated smooth muscle progenitors, either systemically, or locally into a patient suffering from ED. Specific methods of inducing generating smooth muscle progenitors from embryonic stem cell include: purifying and expanding said progenitors from embryoid bodies, culturing of stem cell lines in agents known to induce differentiation along the smooth muscle lineage, such as TGF-b, PDGF, and FGF-4 Assessment of differentiation can be performed using markers of smooth muscle cells known in the art, such as smooth muscle alpha-actin. Administration of cells may be performed as described above in terms of formulations and co-factors to promote migration to area of need.

In another embodiment embryonic stem cells are differentiated into a desired phenotype microencapsulated so as to retain viability and ability to produce growth factors, while at the same time escaping immune mediated killing. This may be accomplished using known microencapsulation methods described in the art, such as described in U.S. Pat. No. 7,041,634 to Weber et al, or US Patent Application No. 2004/0136971 to Scharp et al, each of which is incorporated by reference herein in its entirety. Additionally, embryonic stem cells may be irradiated either prior to, or subsequent to, encapsulation so as to block ability to proliferate while retaining growth factor producing activity.

In another embodiment embryonic stem cells are grown on the outside of a hollow-fiber filter which is connected to a continuous extracorporeal system. Said hollow-fiber system contains pores in the hollow fiber of sufficient size so has to allow exchange of proteins between circulating blood cells and cultured cells on the outside of the hollow fibers, without interchange of host cells with the embryonic stem cells.

Cord Blood Stem Cells

In another embodiment of the invention cord blood stem cells are administered systemically into a patient suffering from erectile dysfunction. Said cord blood stem cells may be administered as a heterogenous population of cells by the administration of cord blood mononuclear cells. Said cells may be isolated according to many methods known in the art. In one particular method, cord blood is collected from fresh placenta and mononuclear cells are purified by centrifugation using a density gradient such as Ficoll or Percoll, in another method cord blood mononuclear cells are isolated from contaminating erythrocytes and granulocytes by the Hetastarch with a 6% (wt/vol) hydroxyethyl starch gradient. Cells are subsequently washed to remove contaminating debris, assessed for viability, and administered at a concentration and frequency sufficient to induce therapeutic benefit.

In another embodiment of the invention, cord blood stem cells are fractionated and the fraction with enhanced therapeutic activity is administered to the patient. Enrichment of cells with therapeutic activity may be performed using physical differences, electrical potential differences, differences in uptake or excretion of certain compounds, as well as differences in expression marker proteins. Distinct physical property differences between stem cells with high proliferative potential and low proliferative potential are known. Accordingly, in some embodiments of the invention, it will be useful to select cord blood stem cells with a higher proliferative ability, whereas in other situations, a lower proliferative ability may be desired. In some embodiments of the invention, cells are directly injected into the area of need, such as in the corpora cavernosa, in which case it will be desirable for said stem cells to be substantially differentiated, whereas in other embodiments, cells will be administered systemically and it this case with may be desirable for the administered cells to be less differentiated, so has to still possess homing activity to the area of need. In embodiments of the invention where specific cellular physical properties are the basis of differentiating between cord blood stem cells with various biological activities, discrimination on the basis of physical properties can be performed using a Fluorescent Activated Cell Sorter (FACS), through manipulation of the forward scatter and side scatter settings. Other methods of separating cells based on physical properties include the use of filters with specific size ranges, as well as density gradients and pheresis techniques.

When differentiation is desired based on electrical properties of cells, techniques such as electrophotoluminescence may be used in combination with a cell sorting means such as FACS. Selection of cells based on ability to uptake certain compounds can be performed using, for example, the ALDE-SORT system, which provides a fluorescent-based means of purifying cells with high aldehyde dehydrogenase activity. Cells with high levels of this enzyme are known to possess higher proliferative and self-renewal activities in comparison to cells possessing lower levels. Other methods of identifying cells with high proliferative activity includes identifying cells with ability to selectively efflux certain dyes such as rhodamine-123 and or Hoechst 33342. Without being bound to theory, cells possessing this property often express the multidrug resistance transport protein ABCG2, and are known for enhanced regenerative ability compared to cells which do not possess this efflux mechanism. In other embodiments cord blood cells are purified for certain therapeutic properties based on expression of markers. In one particular embodiment, cord blood cells are purified for the phenotype of endothelial precursor cells. Said precursors, or progenitor cells express markers such as CD133, and/or CD34. Said progenitors may be purified by positive or negative selection using techniques such as magnetic activated cell sorting (MACS), affinity columns, FACS, panning, or by other means known in the art. Cord blood derived endothelial progenitor cells may be administered directly into the target tissue for ED, or may be administered systemically. Another variation of this embodiment is the use of differentiation of said endothelial precursor cells in vitro, followed by infusion into a patient. Verification for endothelial differentiation may be performed by assessing ability of cells to bind FITC-labeled Ulex europaeus agglutinin-1, ability to endocytose acetylated Di-LDL, and the expression of endothelial cell markers such as PECAM-1, VEGFR-2, or CD31.

Certain desired activities can be endowed onto said cord blood stem cells prior to administration into the patient. In one specific embodiment cord blood cells may be "activated" ex vivo by a brief culture in hypoxic conditions in order to upregulate nuclear translocation of the HIF-1 transcription factor and endow said cord blood cells with enhanced angiogenic potential. Hypoxia may be achieved by culture of cells in conditions of 0.1% oxygen to 10% oxygen, preferably between 0.5% oxygen and 5% oxygen, and more preferably around 1% oxygen. Cells may be cultured for a variety of timepoints ranging from 1 hour to 72 hours, more preferably from 13 hours to 59 hours and more preferably around 48 hours. Assessment of angiogenic, and other desired activities usefull for the practice of the current invention, can be performed prior to administration of said cord blood cells into the patient. Assessment methods are known in the art and include measurement of angiogenic factors, ability to support viability and activity of cells associated with erectile function, as well as ability to induce regeneration of said cellular components associated with erectile function.

In addition to induction of hypoxia, other therapeutic properties can be endowed unto cord blood stem cells through treatment ex vivo with factors such as de-differentiating compounds, proliferation inducing compounds, or compounds known to endow and/or enhance cord blood cells to possess properties useful for the practice of the current invention. In one embodiment cord blood cells are cultured with an inhibitor of the enzyme GSK-3 in order to enhance expansion of cells with pluripotent characteristics while not increasing the rate of differentiation. In another embodiment, cord blood cells are cultured in the presence of a DNA methyltransferase inhibitor such as 5-azacytidine in order to endow a "de-differentiation" effect. In another embodiment cord blood cells are cultured in the presence of a differentiation agent that skews said cord blood stem cells to generate enhance numbers of cells which are useful for treatment of ED after said cord blood cells are administered into a patient. For example, cord blood cells may be cultured in testosterone for a brief period so that subsequent to administration, an increased number of cavernousal smooth muscle cells are generated in the patient in need thereof.

Placental Stem Cells

In contrast to cord blood stem cells, placental stem cells may be purified directly from placental tissues, said tissues including the chorion, amnion, and villous stroma [78, 79]. In another embodiment of the invention, placental tissue is mechanically degraded in a sterile manner and treated with enzymes to allow dissociation of the cells from the extracellular matrix. Such enzymes include, but not restricted to trypsin, chymotrypsin, collagenases, elastase and/or hylauronidase. Suspension of placental cells are subsequently washed, assessed for viability, and may either be used directly for the practice of the invention by administration either locally or systemically. Alternatively, cells may be purified for certain populations with increased biological activity. Purification may be performed using means known in the art, and described above for purification of cord blood stem cells, or may be achieved by positive selection for the following markers: SSEA3, SSEA4, TRA1-60, TRA1-81, c-kit, and Thy-1. In some situations it will be desirable to expand cells before introduction into the human body. Expansion can be performed by culture ex vivo with specific growth factors [80, 81]. The various embodiments of the invention described above for cord blood and embryonic stem cells can also be applied for placental stem cells.

Bone Marrow Stem Cells

Bone marrow stem cells may be used either freshly isolated, purified, or subsequent to ex vivo culture. A typical bone marrow harvest for collecting starting material for practicing one embodiment of the invention involves a bone marrow harvest with the goal of acquiring approximately 5-700 ml of bone marrow aspirate. Numerous techniques for the aspiration of marrow are described in the art and part of standard medical practice. One particular methodology that may be attractive due to decreased invasiveness is the "minibone marrow harvest" [82]. Said aspirate is used as a starting material for purification of cells with ED-inhibitory activity. In one specific embodiment bone marrow mononuclear cells are isolated by pheresis or gradient centrifugation. Numerous methods of separating mononuclear cells from bone marrow are known in the art and include density gradients such as Ficoll Histopaque at a density of approximately 1.077 g/ml or Percoll gradient. Separation of cells by density gradients is usually performed by centrifugation at approximately 450 g for approximately 25-60 minutes. Cells may subsequently be washed to remove debris and unwanted materials. Said washing step may be performed in phosphate buffered saline at physiological pH. An alternative method for purification of mononuclear cells involves the use of apheresis apparatus such as the CS3000-Plus blood-cell separator (Baxter, Deerfield, USA), the Haemonetics separator (Braintree, Mass.), or the Fresenius AS 104 and the Fresenius AS TEC 104 (Fresenius, Bad Homburg, Germany) separators. In addition to injection of mononuclear cells, purified bone marrow sub-populations may be used. Additionally, ex vivo expansion and/or selection may also be utilized for augmentation of desired biological properties for use in treatment of ED. The various embodiments of the invention described above for cord blood and embryonic stem cells can also be applied for bone marrow stem cells.

Amniotic Fluid Stem Cells

Amniotic fluid is routinely collected during amniocentesis procedures. One method of practicing the current invention is utilizing amniotic fluid derived stem cells for treatment of ED. In one embodiment amniotic fluid mononuclear cells are utilized therapeutically in an unpurified manner. Said amniotic fluid stem cells are administered either locally or systemically in a patient suffering from ED. In other embodiments amniotic fluid stem cells are substantially purified based on expression of markers such as SSEA-3, SSEA4, Tra-1-60, Tra-1-81 and Tra-2-54, and subsequently administered. In other embodiments cells are cultured, as described in US Patent Application No. 2005/0054093 (incorporated by reference herein in its entirety), expanded, and subsequently infused into the patient. Amniotic stem cells are described in the following references [83-85]. One particular aspect of amniotic stem cells that makes them amenable for use in practicing certain aspects of the current invention is their bi-phenotypic profile as being both mesenchymal and neural progenitors [86]. This property is usefull for treatment of patients with ED in which neural regeneration is required to a greater extent than vascular repair. The various embodiments of the invention described above for cord blood and embryonic stem cells can also be applied for amniotic fluid stem cells.

Neuronal Stem Cells

Stem cells committed to the neuronal lineage, or neuronal progenitor cells, are used in the practice of some specific embodiments of the invention. Said cells may be generated by differentiation of embryonic stem cells, may be freshly isolated from fetal tissue (ie mesencephalic), may be generated by transdifferentiation, or by reprogramming of a cell. Neuronal progenitors are selected by use of markers such as polysialyated N-CAM, N-CAM, A2B5, nestin and vimentin. The various embodiments of the invention described above for cord blood and embryonic stem cells can also be applied for neuronal stem cells.

Circulating Peripheral Blood Stem Cells

A wide variety of stem cells are known to circulate in the periphery. These include multipotent, pluripotent, and committed stem cells. In some embodiments of the invention mobilization of stem cells is induced in order to increase the number of circulating stem cells, so that harvesting efficiency is increased. Said mobilization allows for harvest of cells with desired properties for practice of the invention without the need to perform bone marrow puncture. A variety of methods to induce mobilization are known. Methods such as administration of cytotoxic chemotherapy, for example, cyclophosphamide or 5-fluoruracil are effective but not preferred in the context of the current invention due to relatively unacceptable adverse events profile. Suitable agents useful for mobilization include: granulocyte colony stimulating factor (G-CSF), granulocyte-macrophage colony stimulating factor (GM-CSF), interleukin 1 (IL-1), interleukin 3 (IL-3), stem cell factor (SCF, also known as steel factor or kit ligand), vascular endothelial growth factor (VEGF), Flt-3 ligand, platelet-derived growth factor (PDGF), epidermal growth factor (EGF), fibroblast growth factor-1 (FGF-1), fibroblast growth factor-2 (FGF-2), thrombopoietin (TPO), interleukin-11 (IL-11), insulin-like growth factor-1 (IGF-1), megakaryocyte growth and development factor (MGDF), nerve growth factor (NGF), hyperbaric oxygen, and 3-hydroxy-3-methyl glutaryl coenzyme A (HMG CoA)reductase inhibitors. The various embodiments of the invention described above for cord blood and embryonic stem cells can also be applied for circulating peripheral blood stem cells.

In a preferred embodiment, donors (either autologous or allegeneic) are mobilized by administration of G-CSF (filgrastim: neupogen) at a concentration of 10 ug/kg/day by subcutaneous injection for 2-7 days, more preferably 4-5 days. Peripheral blood mononuclear cells are collected using an apheresis device such as the AS104 cell separator (Fresenius Medical). $1-40 \times 10^9$ mononuclear cells are collected, concentrated and injected into the area of penile flow occlusion in an intramuscular manner. Alternatively, cells may be injected systemically, or in an area proximal to the region of penile blood flow occlusion. Identification of such occlusion is routinely known in the art and includes the use of penile ultrasonometry. Variations of this procedure may include steps such as subsequent culture of cells to enrich for various populations known to possess angiogenic and/or neurogenic, and/or anti-atrophy Additionally cells may be purified for specific subtypes before and/or after culture. Treatments can be made to the cells during culture or at specific timepoints during ex vivo culture but before infusion in order to generate and/or expand specific subtypes and/or functional properties.

Mesenchymal Stem Cells

In one embodiment mesenchymal cells are generated through culture. For example, U.S. Pat. No. 5,486,359 (incorporated by reference herein in its entirety) describes methods for culturing such and expanding mesenchymal stem cells, as well as providing antibodies for use in detection and isolation. U.S. Pat. No. 5,942,225 (incorporated by reference herein in its entirety) teaches culture techniques and additives for differentiation of such stem cells which can be used in the context of the present invention to produce increased numbers of cells with angiogenic capability. Although U.S. Pat. No. 6,387,369 (incorporated by reference herein in its entirety) teaches use of mesenchymal stem cells for regeneration of cardiac tissue, in accordance with published literature [87, 88] stem cells generated through these means are actually angiogenically potent and therefore may be utilized in the context of the current invention for treatment/amelioration of erectile dysfunction. Without being bound to a specific theory or mechanism of action, it appears that mesenchymal stem cells induce angiogenesis through production of factors such as vascular endothelial growth factor, hepatocyte growth factor, adrenomedullin, and insulin-like growth factor-1 [89].

Mesenchymal stem cells are classically obtained from bone marrow sources for clinical use, although this source may have disadvantages because of the invasiveness of the donation procedure and the reported decline in number of bone marrow derived mesenchymal stem cells during aging. Alternative sources of mesenchymal stem cells include adipose tissue [90], placenta [79, 91], scalp tissue [92] and cord blood [93]. A recent study compared mesenchymal stem cells from bone marrow, cord blood and adipose tissue in terms of colony formation activity, expansion potential and immunophenotype. It was demonstrated that all three sources produced mesenchymal stem cells with similar morphology and phenotype. Ability to induce colony formation was highest using stem cells from adipose tissue and interestingly in contrast to bone marrow and adipose derived mesenchymal cells, only the cord blood derived cells lacked ability to undergo adipocyte differentiation. Proliferative potential was the highest with cord blood mesenchymal stem cells which were capable of expansion to approximately 20 times, whereas adipose derived mesenchymal cells expanded an average of 8 times and bone marrow derived cells expanded 5 times [94].

Accordingly, one skilled in the art will understand that mesenchymal stem cells for use with the present invention may be selected upon individual patient characteristics and the end result sought. For example, if autologous mesenchymal stem cells are available in the form of adipocyte-derived cells, it will be useful to utilize this source instead of allogeneic cord-blood derived cells. Alternatively, cord blood derived mesenchymal stem cells may be more advantageous for use in situations where autologous cells are not available, and expansion is sought.

The ability of mesenchymal stem cells from the cord blood to expand in vitro also allows the possibility of genetically modifying these cells in order to: a) decrease immunogenicity; b) enhance angiogenic potential; and c) augment survival following administration. However it should be noted that such ex vivo manipulation is applicable to all cell types described in the current application.

In situations where a decrease in immunogenicity is sought, cells may be transfected using immune suppressive agents. Said agents include soluble factors, membrane-bound factors, and enzymes capable of causing localized immune suppression. Examples of soluble immune suppressive factors include: IL-4 [95], IL-10 [96], IL-13 [97], TGF-b [98], soluble TNF-receptor [99], and IL-1 receptor agonist [100]. Membrane-bound immunoinhibitor molecules that may be transfected into stem cells for use in practicing the current invention include: HLA-G [101], FasL [102], PD-1L [103], Decay Accelerating Factor [104], and membrane-associated TGF-b [105]. Enzymes which may be transfected in order to cause localized immune suppression include indolamine 2,3 dioxygenase [106] and arginase type II [107]. In order to optimize desired immune suppressive ability, a wide variety of assays are known in the art, including mixed lymphocyte culture, ability to generate T regulatory cells in vitro, and ability to inhibit natural killer or CD8 cell cytotoxicity.

In situations where increased angiogenic potential of said mesenchymal stem cells is desired, mesenchymal stem cells may be transfected with genes such as VEGF[108], FGF1 [109], FGF2 [110], FGF4 [111], FrzA [112], and angiopoietin [113]. Ability to induce angiogenesis may be assessed in vitro prior to administration of said transfected cells in vivo. Methods of assessing in vitro angiogenesis stimulating ability are well known in the art and include measuring proliferation of human umbilical vein derived endothelial cells.

Since one of the problems of cell therapy in general is viability of the infused cells subsequent to administration, it may be desired in some forms of the invention to transfect mesenchymal cells with genes protecting said cells from apoptosis. Anti-apoptotic genes suitable for transfection may include bcl-2 [114], bcl-x1 [115], and members of the XIAP family [116]. Alternatively it may be desired to increase the proliferative lifespan of said mesenchymal stem cells through transfection with enzymes associated with anti-senescence activity. Said enzymes may include telomerase or histone deacetylases. The various embodiments of the invention described above for cord blood and embryonic stem cells can also be applied for mesenchymal stem cells.

Adipose Tissue Derived Stem Cells

Adipose derived stem cells express markers such as CD9; CD29 (integrin beta 1); CD44 (hyaluronate receptor); CD49d,e (integrin alpha 4, 5); CD55 (decay accelerating factor); CD105 (endoglin); CD106 (VCAM-1); CD166 (ALCAM). These markers are useful not only for identification but may be used as a means of positive selection, before and/or after culture in order to increase purity of the desired cell population. In terms of purification and isolation, devices are known to those skilled in the art for rapid extraction and purification of cells adipose tissues. U.S. Pat. No. 6,316,247 (incorporated by reference herein in its entirety) describes a device which purifies mononuclear adipose derived stem cells in an enclosed environment without the need for setting up a GMP/GTP cell processing laboratory so that patients may be treated in a wide variety of settings. One embodiment of the invention involves attaining 10-200 ml of raw lipoaspirate, washing said lipoaspirate in phosphate buffered saline, digesting said lipoaspirate with 0.075% collagenase type I for 30-60 min at 37° C. with gentle agitation, neutralizing said collagenase with DMEM or other medium containing autologous serum, preferably at a concentration of 10% v/v, centrifuging the treated lipoaspirate at approximately 700-2000 g for 5-15 minutes, followed by resuspension of said cells in an appropriate medium such as DMEM. Cells are subsequently filtered using a cell strainer, for example a 100 µm nylon cell strainer in order to remove debris. Filtered cells are subsequently centrifuged again at approximately 700-2000 g for 5-15 minutes and resuspended at a concentration of approximately $1\times10^6/cm^2$ into culture flasks or similar vessels. After 10-20 hours of culture non-adherent cells are removed by washing with PBS and remaining cells are cultured at similar conditions as described above for culture of cord blood derived mesenchymal stem cells. Upon reaching a concentration desired for clinical use, cells are harvested, assessed for purity and administered in a patient in need thereof as described above. The various embodiments of the invention described above for cord blood and embryonic stem cells can also be applied for adipose derived stem cells.

Exfoliated Teeth Derived Stem Cells

Deciduous teeth (baby teeth) have been recently identified as a source of pluripotent stem cells with ability to differentiate into endothelial, neural, and bone structures. Said pluripotent stem cells have been termed "stem cells from human exfoliated deciduous teeth" (SHED). One of the embodiments of the current invention involves utilization of this novel source of stem cells for the treatment of ED. In one embodiment of the invention, SHED cells are administered systemically or locally into a patient with ED at a concentration and frequency sufficient for induction of therapeutic effect. SHED cells can be purified and used directly, certain sub-populations may be concentrated, or cells may be expanded ex vivo under distinct culture conditions in order to generate phenotypes desired for maximum therapeutic effect. Growth and expansion of SHED has been previously described by others. In one particular method, exfoliated human deciduous teeth are collected from 7- to 8-year-old children, with the pulp extracted and digested with a digestive enzyme such as collagenase type I. Concentrations necessary for digestion are known and may be, for example 1-5 mg/ml, or preferable around 3 mg/ml. Additionally dispase may also be used alone or in combination, concentrations of dispase may be 1-10 mg/ml, preferably around 4 mg/ml. Said digestion is allowed to occur for approximately 1 h at 37° C. Cells are subsequently washed and may be used directly, purified, or expanded in tissue culture. The various embodiments of the invention described above for cord blood and embryonic stem cells can also be applied for exfoliated teeth stem cells.

Hair Follicle Stem Cells

The bulge area of the hair follicle bulge is an easily accessible source of pluripotent mesenchymal-like stem cells. One embodiment of the current invention is the use of hair follicle stem cells for treatment of ED. Said cells may be used therapeutically once freshly isolated, or may be purified for particular sub-populations, or may be expanded ex vivo prior to use. Purification of hair follicle stem cells may be performed from cadavers, from healthy volunteers, or from patients undergoing plastic surgery. Upon extraction, scalp specimens are rinsed in a wash solution such as phosphate buffered saline or Hanks and cut into sections 0.2-0.8 cm. Subcutaneous tissue is de-aggregated into a single cell suspension by use of enzymes such as dispase and/or collagenase. In one variant, scalp samples are incubated with 0.5% dispase for a period of 15 hours. Subsequently, the dermal sheath is further enzymatically de-aggregated with enzymes such as collagenase D. Digestion of the stalk of the dermal papilla, the source of stem cells is confirmed by visual microscopy. Single cell suspensions are then treated with media containing fetal calf serum, and concentrated by pelleting using centrifugation. Cells may be further purified for expression of markers such as CD34, which are associated with enhanced proliferative ability. In one embodiment of the invention, collected hair follicle stem cells are induced to differentiate in vitro into neural-like cells through culture in media containing factors such as FGF-1, FGF-2, NGF, neurotrophin-2, and/or BDNF. Confirmation of neural differentiation may be performed by assessment of markers such as Muhashi, polysialyated N-CAM, N-CAM, A2B5, nestin, vimentin glutamate, synaptophysin, glutamic acid decarboxylase, serotonin, tyrosine hydroxylase, and GABA. Said neuronal cells may be administered systemically, or locally in a patient with ED. The various embodiments of the invention described above for cord blood and embryonic stem cells can also be applied for hair follicle stem cells.

Parthenogenically Derived Stem Cells

Parthenogenically derived stem cells can be generated by addition of a calcium flux inducing agent to activate oocytes, followed by purifying and expanding cells expressing embryonic stem cell markers such as SSEA-4, TRA 1-60 and/or TRA 1-81. Said parthenogenically derived stem cells are totipotent and can be used in a manner similar to that described for embryonic stem cells in the practice of the current invention. The various embodiments of the invention described above for cord blood and embryonic stem cells can also be applied for parthenogenically derived stem cells.

Reprogrammed Stem Cells

Reprogramming of non-stem cells to endow them with stem cell characteristics can generate stem cells for use in the practice of the current invention. The advantage of reprogramming cells is that ability to withdraw autologous cells, which may have limited stem cell potential, endow said autologous cells with stem cell, or stem cell-like, properties, and reintroduce said autologous cells into the patient. The various embodiments of the invention described above for cord blood and embryonic stem cells can also be applied for reprogrammed stem cells.

Side Population Stem Cell

Cells expressing the ability to efflux certain dyes, including but not limited to rhodamin-123 are associated with stem cell-like properties. Said cells can be purified from tissue subsequent to cell dissociation, based on efflux properties. Accordingly, in one embodiment of the current invention, tissue derived side population cells may be utilized either freshly isolated, sorted into subpopulations, or subsequent to ex vivo culture, for the treatment of ED. For use in the invention, side population cells may be derived from tissues such as pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue. More optimally, side population cells obtained from smooth muscle tissue are administered at a concentration and frequency sufficient to induce a therapeutic effect on ED. The various embodiments of the invention described above for cord blood and embryonic stem cells can also be applied for side population stem cells.

Injection Steps

In one embodiment of the invention bone marrow mononuclear cells are concentrated in an injection solution, which may be saline, mixtures of autologous plasma together with saline, or various concentrations of albumin with saline. Ideally pH of the injection solution is from about 6.4 to about 8.3, optimally 7.4. Excipients may be used to bring the solution to isotonicity such as, 4.5% mannitol or 0.9% sodium chloride, pH buffers with art-known buffer solutions, such as sodium phosphate. Other pharmaceutically acceptable agents can also be used to bring the solution to isotonicity, including, but not limited to, dextrose, boric acid, sodium tartrate, propylene glycol, polyols (such as mannitol and sorbitol) or other inorganic or organic solutes.

Therapeutic Embodiment

It is known that testosterone administration is useful for treatment of ED in patients suffering from hypogonadism [117]. However testosterone mediated improvement of erectile function in patients with basal level of testosterone who suffer from ED is not clearly established. One embodiment of the current invention capitalizes on the observation that testosterone is capable of inducing stem cell differentiation into smooth muscle tissue. Specifically, it is known that CD34+ stem cells are capable of differentiating into a variety of muscle lineages upon treatment with testosterone [118]. Additionally, testosterone is capable of modulating endothelial function by increasing responsiveness to dilation stimuli [119], as well as upregulation of ability to generate and respond to NO [120]. Accordingly, in one specific embodiment testosterone is administered to a patient suffering from ED in combination with administration of stem cells. This therapy is performed with the end goal of simultaneously increasing the mass of smooth muscle cells in the penile area, as well as providing endothelial cell progenitors that can increase localized blood flow to the penile area. Administration of testosterone may be performed either systemically, or in a more preferred embodiment, locally. Administration of stem cells may be performed locally or systemically, with the preferred embodiment depending on individual patient characteristics. In some situations, patients with ED are treated with localized testosterone gel administered topically on the penile skin. In other embodiments, testosterone may be administered by urethral suppository or by intracavernous injection. Testosterone may be administered in the form of a precursor or a chemical modified form which possesses androgenic activity. Concentrations of testosterone to be administered vary on patient characteristics and route of administration, but may include concentrations of 1-10 mg/day applied 1-4 times per day when applied topically on penile skin. More preferably, concentrations may range from 3-5 mg/day applied 1-3 times per day. Even more preferably, concentrations may be approximately 4 mg/day applied twice per day. In some embodiments of the invention stem cell administration is performed through intravenous injection of autologous, allogeneic or xenogeneic stem cells. In one preferred embodiment allogeneic cord blood stem cells are administered either as mononuclear cells or as purified stem cells. In a more preferred embodiment cord blood mononuclear cells are selected for expression of markers of the angiogenesis supporting phenotype such as CD133. Said cells are administered at a concentration sufficient to cause increased smooth muscle mass and angiogenesis in the penile area. Concentration of CD133 cells administered may range from $1\times10^6$-$10\times10^7$ cells, but more preferably between $1\times10^6$-$5\times10^7$ cells and even more preferably between $1\times10^6$-$1\times10^7$ cells. Stem cell administration may be performed as a single event or may be performed in multiple cycles depending on functional result obtained, as well as individual patient characteristics. Efficacy of stem cell therapy may be quantified using standard scales of sexual and erectile function, as well as more objective techniques such as Doppler ultrasonography, angiography or nerve-mediated erectile stimulation.

EXAMPLES

The following examples are offered to illustrate, but not to limit, the claimed invention. These examples are given to enable those of ordinary skill in the art to more clearly understand and to practice the present invention. The examples should not be considered as limiting the scope of the invention, but merely as be illustrative and representative thereof.

Example 1

Increased Sexual Potency in Critical Limb Ischemia Patients Treated with CD34+ Stem Cells 17 patients suffering from Fountain III and IV critical limb ischemia are selected for stem cell therapy based on non-responsiveness to medical interventions and ineligibility for surgical intervention. Inclusion into the study require measurable haemodynamic deficits including a resting ankle-brachial pressure index (ABI) less than 0·5 in the effected limb on two consecutive examinations done at least 2 weeks apart. Patients with poorly controlled diabetes mellitus (HbA1c>6.4% and proliferative retinopathy) or with evidence of malignant disorder during the past 5 years are excluded due to the potential of bone marrow cells to stimulate angiogenesis.

Patients are subjected to a bone marrow harvest. Briefly, patients are positioned face down on a horizontal platform and provided analgesics as per standard medical procedures. All personnel involved in the procedure are dressed in sterile surgical gowning and masks. The harvesting field comprising both iliac crests is prepared by topically applying standard disinfectant solution. Iliac crests are anaesthetized and the harvesting needle is inserted in order to puncture the iliac crest. The cap and stylet of the harvesting needle is removed and 3-ml of marrow is harvested into the 15-ml harvesting syringe containing heparin solution. The process is repeated and the contents of the harvesting syringe are transferred into a 500-ml collecting bag. Approximately 75-125 ml of bone marrow is harvested in total.

Isolation of mononuclear cells is performed by gradient separation using the Hetastarch method, which is clinically applicable and reported to remove not only erythrocytes but also granulocytic cells. The previously published method of Montuoro et al is used [121]. Briefly, six-percent (wt/vol) Hetastarch (HES40, Hishiyama Pharmaceutical Co., Osaka, Japan) is added to the collected bone marrow sample to achieve a final concentration of 1.2 percent Hetastarch, (1:5 volume ratio of added Hetastarch to bone marrow). Centrifugation at 50 g for 5 min at 10° C. is performed in order to generate a leukocyte rich supernatant. Sedimentation of bone marrow takes place at a cell concentration of no more than $15\times10^6$ cells/ml in a total volume of 850 ml per Hetastarch bag. The supernatant is transferred into a plasma transfer bag and centrifuged (400 g for 10 min) to sediment the cells. The sedimented cells are subsequently washed in phosphate buffered saline in the presence of 5% penicillin/streptomycin mixture (Gibco, Mississauga, Canada) and 5% autologous serum. Cellular viability and lack of potential contamination with other cells is assessed by microscopy. Bone marrow mononuclear cells are subsequently concentrated and purified for CD133+ cells using the CliniMacs system according to the manufacturer's instructions.

Cells are injected into patients either in the gluteus maximus muscles (10 patients) or in the gastrocnemius muscle (7 patients) at concentrations ranging from $5\times10^6$-$3\times10^7$. Two weeks post cellular administration, increased sexual potency and ability to perform sexually is spontaneously reported in 9 of the 10 patients injected into the gluteus maximus muscles and in none of the 7 patients injected into the gastrocnemius muscle.

Example 2

Treatment of ED by Systemic Administration of Cord Blood Derived Stem Cells 30 patients with ED (IIEF-5 questionnaire score average of 9.5) unresponsive to phosphodiesterase inhibitors are selected for cellular therapy. Said patients are randomized into a placebo and treated groups (15 each).

Umbilical cord blood is purified according to routine methods [122]. Briefly, a 16-gauge needle from a standard Baxter 450-ml blood donor set containing CPD A anticoagulant (citrate/phosphate/dextrose/adenine) (Baxter Health Care, Deerfield, Ill.) is inserted and used to puncture the umbilical vein of a placenta obtained from healthy delivery from a mother tested for viral and bacterial infections according to international donor standards. Cord blood is allowed to drain by gravity so as to drip into the blood bag. The placenta is placed in a plastic-lined, absorbent cotton pad suspended from a specially constructed support frame in order to allow collection and reduce the contamination with maternal blood and other secretions, The 63 ml of CPD A used in the standard blood transfusion bag, calculated for 450 ml of blood, is reduced to 23 ml by draining 40 ml into a graduated cylinder just prior to collection. This volume of anticoagulant matches better the cord volumes usually retrieved (<170 ml).

An aliquot of the blood is removed for safety testing according to the standards of the National Marrow Donor Program (NMDP) guidelines. Safety testing includes routine laboratory detection of human immunodeficiency virus 1 and 2, human T-cell lymphotropic virus I and II, Hepatitis B virus, Hepatitis C virus, Cytomegalovirus and Syphilis. Subsequently, 6% (wt/vol) hydroxyethyl starch is added to the anticoagulated cord blood to a final concentration of 1.2%. The leukocyte rich supernatant is then separated by centrifuging the cord blood hydroxyethyl starch mixture in the original collection blood bag ($50\times$g for 5 min at 10° C.). The leukocyte-rich supernatant is expressed from the bag into a 150-ml Plasma Transfer bag (Baxter Health Care) and centrifuged ($400\times$g for 10 min) to sediment the cells. Surplus supernatant plasma is transferred into a second plasma Transfer bag without severing the connecting tube. Finally, the sedimented leukocytes are resuspended in supernatant plasma to a total volume of 20 ml. Approximately $5\times10^8$-$7\times10^9$ nucleated cells are obtained per cord. Cells are cryopreserved according to the method described by Rubinstein et al [122] for subsequent cellular therapy.

Patients are HLA-matched to HLA-A and HLA-B using serotyping and to HLA-DR using genetic analysis. Patients are matched to the cord blood to 2 HLA-loci. Upon identification of suitable donor cord blood cells, cells are thawed, and assessed for viability and purity according to the method published by Rubinstein et al [122]. Cells are washed and concentrated to a volume of 10 ml in UPS saline with 5% autologous serum. Total cell injection number is $5 \times 10^8$ per patient. Cells are administered into systemic circulation over a period of 1 hour. Patients are observed for adverse events for the first 12 hours subsequent to administration and subsequently discharged. Control patients are administered a placebo injection of saline. Infusion bags are covered so as to make it impossible to distinguish between patients receiving cell therapy or saline. At two weeks post injection all patients are asked to complete the IIEF-5 questionnaire. Treated patients report an average score of 18.5, whereas control patients report a score of 10.4. No treatment associated adverse events are reported. Analysis of penile blood flow using doppler angiography identifies a marked increase in penile perfusion in the treated group compared to controls. A correlation is seen between increased penile perfusion and responsiveness to flow-mediated endothelium-dependent dilation of the brachial artery during reactive hyperemia.

Example 3

Treatment of ED by Systemic Administration of Cord Blood Derived Stem Cells Together with Localized Testosterone Therapy 30 patients with ED (IIEF-5 questionnaire score average of 10.3) unresponsive to phosphodiesterase inhibitors are selected for cellular therapy. Said patients are randomized into a placebo and treated groups (15 each).

Umbilical cord blood cells are isolated, HLA-matched and administered as described in Example 2. Subsequent to cell administration, testosterone gel (4 mg/day; supplied by Azupharma, Germany) is applied to the penile skin twice a day over a period of 6 weeks in both control and stem cell treated groups. The IIEF-5 questionnaire is administered at 2, 6, and 12 weeks post-cellular infusion. Patients in the placebo group report an average of 11.5, 10.9, and 11.1 score for weeks 2, 6, and 12, respectively. Patients in the cell therapy group report an average 20.2, 23.4, and 22.4 score for weeks 2, 6, and 12, respectively.

Example 4

Treatment of ED by Systemic Administration of Cord Blood Derived Mesenchymal Stem Cells Together with Localized Testosterone Therapy 30 patients with ED (IIEF-5 questionnaire score average of 10.3) unresponsive to phosphodiesterase inhibitors are selected for cellular therapy. Said patients are randomized into placebo and treated groups (15 each).

Cord blood is obtained, processed and HLA-matched according to EXAMPLE 2. Cord blood mononuclear cells are seeded at a density of $1 \times 10^6$ cells/cm$^2$ into culture flasks in a Good Manufacturing Procedures-compliant sterile clean room. Cells are cultured in DMEM-LG media (Life Technologies), supplemented with 10% autologous serum. On day 4, nonadherent cells are discarded and fresh tissue culture medium is added. On day 7, cultures are tested for sterility, nonadherent cells are discarded by washing culture flasks with USP saline containing 10% autologous serum, and the remaining adherent cells are washed with Tyrode's Salt Solution (Sigma, St. Louis, Mo.) and incubated for 1 hr in M199 mediua (Life Technologies). Cells are detached with 0.05% trypsin-EDTA (Life Technologies), and are resuspended in M199 supplemented with 10% of autologous serum. Cells are subcultured for 12 days with feeding of cultures performed every 3 days. The cells are subsequently harvested by trypsinization as described above, counted and an aliquot is taken for flow cytometric analyzes for the expression of mesenchymal stem cells markers and lack of expression of hematopoietic markers. Cell batches of >95% purity for CD73, and CD105, and less than 5% contamination of CD45 expressing cells are chosen for cell therapy.

Treated patients are administered $5\text{-}10 \times 10^7$ mesenchymal stem cells intravenously over a period of 4 hours. Placebo control patients receive an injection of saline over the same time period. Subsequently, testosterone gel (4 mg/day; supplied by Azupharma, Germany) is applied to the penile skin twice a day over a period of 6 weeks in both control and stem cell treated groups. The IIEF-5 questionnaire is administered at 2, 6, and 12 weeks post-cellular infusion. Patients in the placebo group report an average of 10.5, 9.9, and 10.1 score for weeks 2, 6, and 12, respectively. Patients in the cell therapy group report an average 24.2, 25.2, and 25.3 score for weeks 2, 6, and 12, respectively.

Example 5

Treatment of ED by Systemic Administration of Cord Blood Mesenchymal Stem Cell Derived Supernatant Concentrate Cord blood mesenchymal stem cells are generated as described in Example 4. Said mesenchymal stem cells are assessed for purity based on expression of CD73, and CD105 and cultured at a concentration of $1 \times 10^6$ cells/cm$^2$ in AIM-V media containing 5% human serum under conditions of hypoxia with 1% $O_2$ for 48 hours. Supernatant is collected, filter-sterilized using a 0.2 micron filter, dialyzed to remove salts and low molecular weight electrolytes, and reconstituted in injectable saline. Quantification of angiogenic activity is performed by addition of various amounts of concentrated supernatant into a standard culture of human umbilical vein endothelial cells (HUVEC). The amount of concentrated supernatant capable of stimulating proliferation of $5 \times 10^5$ HUVEC cells by 50% compared to control cultures is termed "1 Unit".

30 patients with ED (IIEF-5 questionnaire score average of 7.5) unresponsive to phosphodiesterase inhibitors are selected for therapy with stem cell product. Said patients are randomized into a placebo and treated groups (15 each). Patients in the treated group are administered a systemic dose of $10^4$ Units per kg, whereas controls receive saline. Administration is performed twice weekly for a period of 4 weeks. At completion of treatment patient erectile function is assessed by the IIEF-5 questionnaire. Patients receiving saline control report an average IIEF-5 score of 8.1, whereas patients receiving supernatant concentrate report a score of 25.3.

Example 6

Treatment of ED by Systemic Administration of Adipose Stem Cell Derived Supernatant Concentrate Subcutaneous adipose tissue samples are obtained from a plastic surgery clinic under good tissue practice guidelines in a sterile manner from liposuction procedure material. Adipose tissue is digested in collagenase type I solution under gentle agitation for 1.5 hours at 37° C., filtered with 500-μm and 250-μm Nitex filters, and centrifuged at 200 g for 5 minutes to separate the stromal cell fraction (mesenchymal progenitors) from adipocytes. The cells are treated with erythrocyte lysis buffer for 5 minutes at 37° C., then centrifuged at 300 g for 5 minutes. The supernatant is discarded, and the cell pellet is resuspended in AIM-V media supplemented with 5% human serum at a concentration of $1\times10^5$ cells/$cm^2$. Cells are exposed to hypoxic conditions for 48 hours at 1% oxygen. Supernatant is collected, concentrated, and quantified as described in Example 5.

30 patients with ED (IIEF-5 questionnaire score average of 8.2) unresponsive to phosphodiesterase inhibitors are selected for therapy with stem cell product. Said patients are randomized into a placebo and treated groups (15 each). Patients in the treated group are administered a systemic dose of $10^4$ Units per kg, whereas controls receive saline. Administration is performed twice weekly for a period of 4 weeks. At completion of treatment patient erectile function is assessed by the IIEF-5 questionnaire. Patients receiving saline control report an average IIEF-5 score of 10.2, whereas patients receiving supernatant concentrate report a score of 23.3.

Example 7

Treatment of ED by Systemic Administration of Adipose Stem Cell Derived Supernatant Concentrate Together with Localized Testosterone Therapy Mesenchymal stem cell conditioned media is generated as described in Example 6. 30 patients with ED (IIEF-5 questionnaire score average of 8.4) unresponsive to phosphodiesterase inhibitors are selected for therapy with stem cell product. Said patients are randomized into a placebo and treated groups (15 each). Patients in the treated group are administered a systemic dose of $10^4$ Units per kg, whereas controls receive saline. Administration is performed twice weekly for a period of 4 weeks. Concurrently, testosterone gel (4 mg/day; supplied by Azupharma, Germany) is applied to the penile skin twice a day over a period of 4 weeks in both control and stem cell treated groups. At completion of treatment patient erectile function is assessed by the IIEF-5 questionnaire. Patients receiving saline control report an average IIEF-5 score of 12.2, whereas patients receiving supernatant concentrate report a score of 25.3.

Example 8

Treatment of ED by Localized Administration of Testosterone Combined with Endogenous Stem Cell Mobilization 30 patients with ED (IIEF-5 questionnaire score average of 6.4) unresponsive to phosphodiesterase inhibitors are selected for therapy. Said patients are randomized into a placebo and treated groups (15 each). Patients in the treated group are exposed to 2.0 atmospheres absolute (ATA) O(2) for 2 h per day in a hyperbaric chamber for a period of 1 week, whereas control patients are also placed into a hyperbaric chamber but not exposed to oxygen. At the initiation of hyperbaric oxygen therapy, both the treated and placebo groups apply testosterone gel (4 mg/day; supplied by Azupharma, Germany) to the penile skin twice a day over a period of 4 weeks. At completion of treatment patient erectile function is assessed by the IIEF-5 questionnaire. Patients receiving placebo therapy report an average IIEF-5 score of 7.3, whereas patients receiving hyperbaric oxygen stem cell mobilization report a score of 20.3.

One skilled in the art will appreciate that these methods and devices are and may be adapted to carry out the objects and obtain the ends and advantages mentioned, as well as those inherent therein. The methods, procedures, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. It will be apparent to one skilled in the art that varying substitutions and modifications may be made to the invention disclosed herein without departing from the scope and spirit of the invention. Those skilled in the art recognize that the aspects and embodiments of the invention set forth herein may be practiced separate from each other or in conjunction with each other. Therefore, combinations of separate embodiments are within the scope of the invention as disclosed herein. All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure.

REFERENCES

Each of the following references which are mentioned above is hereby incorporated by reference in its entirety.
1. Kleinman, K. P., et al., *A new surrogate variable for erectile dysfunction status in the Massachusetts male aging study.* J Clin Epidemiol, 2000. 53(1): p. 71-8.
2. Bin Lim, K. and G. B. Brock, *The Erectile Function Visual Analog Scale (EF-VAS): a disease-specific utility instrument for the assessment of erectile function.* Can J Urol, 2006. 13(2): p. 3026.
3. Karakiewicz, P., et al., *Reliability of remembered International Index of Erectile Function domain scores in men with localized prostate cancer.* Urology, 2005. 65(1): p. 131-5.
4. Foresta, C., et al., *Erectile dysfunction: symptom or disease?* J Endocrinol Invest, 2004. 27(1): p. 80-95.
5. Temel, Y., et al., *Role of the brain in the control of erection.* Asian J Androl, 2006. 8(3): p. 259-64.

6. Dua, S. and P. D. Maclean, *Localization for Penile Erection in Medial Frontal Lobe.* Am J Physiol, 1964. 207: p. 1425-34.
7. Park, K., et al., *A new potential of blood oxygenation level dependent (BOLD) functional MRI for evaluating cerebral centers of penile erection.* Int J Impot Res, 2001. 13(2): p. 73-81.
8. Vandewalle, V., et al., *Stereotactic treatment of Gilles de la Tourette syndrome by high frequency stimulation of thalamus.* Lancet, 1999. 353(9154): p. 724.
9. Montorsi, F., et al., *Apomorphine-induced brain modulation during sexual stimulation: a new look at central phenomena related to erectile dysfunction.* Int J Impot Res, 2003. 15(3): p. 203-9.
10. Dieckmann, G. and R. Hassler, *Unilateral hypothalamotomy in sexual delinquents. Report on six cases.* Confin Neurol, 1975. 37(1-3): p. 177-86.
11. Stief, C. G., et al., *The influence of anterior root stimulation (S2) in deafferented spinal cord injury men on cavernous electrical activity.* J Urol, 1992. 148(1): p. 107-10.
12. Giuliano, F. and O. Rampin, *Neural control of erection.* Physiol Behav, 2004. 83(2): p. 189-201.
13. Lin, C. S., G. Lin, and T. F. Lue, *Cyclic nucleotide signaling in cavernous smooth muscle.* J Sex Med, 2005. 2(4): p. 478-91.
14. Burnett, A. L., *Phosphodiesterase 5 mechanisms and therapeutic applications.* Am J Cardiol, 2005. 96(12B): p. 29M-31M.
15. Ganz, P., *Erectile dysfunction: pathophysiologic mechanisms pointing to underlying cardiovascular disease.* Am J Cardiol, 2005. 96(12B): p. 8M-12M.
16. Jones, R. W., et al., *Oxygen free radicals and the penis.* Expert Opin Pharmacother, 2002. 3(7): p. 889-97.
17. Bivalacqua, T. J., et al., *Superoxide anion production in the rat penis impairs erectile function in diabetes: influence of in vivo extracellular superoxide dismutase gene therapy.* J Sex Med, 2005. 2(2): p. 187-97; discussion 197-8.
18. Bakris, G. L., et al., *Advanced glycation end-product cross-link breakers. A novel approach to cardiovascular pathologies related to the aging process.* Am J Hypertens, 2004. 17(12 Pt 2): p. 23S-30S.
19. Basta, G., A. M. Schmidt, and R. De Caterina, *Advanced glycation end products and vascular inflammation: implications for accelerated atherosclerosis in diabetes.* Cardiovasc Res, 2004. 63(4): p. 582-92.
20. Basta, G., et al., *At least 2 distinct pathways generating reactive oxygen species mediate vascular cell adhesion molecule-1 induction by advanced glycation end products.* Arterioscler Thromb Vasc Biol, 2005. 25(7): p. 1401-7.
21. Rashid, G., et al., *Effect of advanced glycation end-products on gene expression and synthesis of TNF-alpha and endothelial nitric oxide synthase by endothelial cells.* Kidney Int, 2004. 66(3): p. 1099-106.
22. Bivalacqua, T. J., et al., *Increased expression of arginase II in human diabetic corpus cavernosum: in diabetic-associated erectile dysfunction.* Biochem Biophys Res Commun, 2001. 283(4): p. 923-7.
23. Akingba, A. G. and A. L. Burnett, *Endothelial nitric oxide synthase protein expression, localization, and activity in the penis of the alloxan-induced diabetic rat.* Mol Urol, 2001. 5(4): p. 189-97.
24. Zhang, X. H., et al., *Testosterone restores diabetes-induced erectile dysfunction and sildenafil responsiveness in two distinct animal models of chemical diabetes.* J Sex Med, 2006. 3(2): p. 253-64; discussion 264-5, author reply 265-6.
25. Wingard, C. J., et al., *Improved erectile function after Rho-kinase inhibition in a rat castrate model of erectile dysfunction.* Am J Physiol Regul Integr Comp Physiol, 2003. 284(6): p. R1572-9.
26. Min, J. K., et al., *Prediction of coronary heart disease by erectile dysfunction in men referred for nuclear stress testing.* Arch Intern Med, 2006. 166(2): p. 201-6.
27. Borgquist, R., et al., *Erectile dysfunction in healthy subjects predicts reduced coronary flow velocity reserve.* Int J Cardiol, 2005.
28. Ponholzer, A., et al., *Is erectile dysfunction an indicator for increased risk of coronary heart disease and stroke?* Eur Urol, 2005. 48(3): p. 512-8; discussion 517-8.
29. Montorsi, P., et al., *The artery size hypothesis: a macrovascular link between erectile dysfunction and coronary artery disease.* Am J Cardiol, 2005. 96(12B): p. 19M-23M.
30. Uslu, N., et al., *Erectile dysfunction as a generalized vascular dysfunction.* J Am Soc Echocardiogr, 2006. 19(3): p. 341-6.
31. Chiurlia, E., et al., *Subclinical coronary artery atherosclerosis in patients with erectile dysfunction.* J Am Coll Cardiol, 2005. 46(8): p. 1503-6.
32. Alkhayal, S., V. Lehmann, and P. Thomas, *A simple non-invasive test to detect vascular disease in patients with erectile dysfunction: a novel method.* J Sex Med, 2006. 3(2): p. 331-6.
33. Giugliano, F., et al., *Erectile dysfunction associates with endothelial dysfunction and raised proinflammatory cytokine levels in obese men.* J Endocrinol Invest, 2004. 27(7): p. 665-9.
34. Seftel, A. D., *Circulating endothelial progenitor cells in subjects with erectile dysfunction.* J Urol, 2005. 174(2): p. 656.
35. Foresta, C., et al., *Circulating endothelial progenitor cells in subjects with erectile dysfunction.* Int J Impot Res, 2005. 17(3): p. 288-90.
36. Foresta, C., et al., *Circulating endothelial progenitor cells and endothelial function after chronic Tadalafil treatment in subjects with erectile dysfunction.* Int J Impot Res, 2006.
37. Mazo, E., S. Gamidov, and V. Iremashvili, *The effect of vardenafil on endothelial function of brachial and cavernous arteries.* Int J Impot Res, 2006.
38. Rosano, G. M., et al., *Chronic treatment with tadalafil improves endothelial function in men with increased cardiovascular risk.* Eur Urol, 2005. 47(2): p. 214-20; discussion 220-2.
39. Dishy, V., et al., *The effect of sildenafil on nitric oxide-mediated vasodilation in healthy men.* Clin Pharmacol Ther, 2001. 70(3): p. 270-9.
40. Vlachopoulos, C., et al., *Type 5 phosphodiesterase inhibition by sildenafil abrogates acute smoking-induced endothelial dysfunction.* Am J Hypertens, 2004. 17(11 Pt 1): p. 1040-4.
41. Laufs, U., et al., *Running exercise of different duration and intensity: effect on endothelial progenitor cells in healthy subjects.* Eur J Cardiovasc Prev Rehabil, 2005. 12(4): p. 407-14.
42. Vasa, M., et al., *Increase in circulating endothelial progenitor cells by statin therapy in patients with stable coronary artery disease.* Circulation, 2001. 103(24): p. 2885-90.
43. Kuwana, M., et al., *Increase in circulating endothelial precursors by atorvastatin in patients with systemic sclerosis.* Arthritis Rheum, 2006. 54(6): p. 1946-1951.
44. Sugawara, J., et al., *Circulating endothelial progenitor cells during human pregnancy.* J Clin Endocrinol Metab, 2005. 90(3): p. 1845-8.

45. Watanabe, T., et al., *Postischemic intraventricular administration of FGF-2 expressing adenoviral vectors improves neurologic outcome and reduces infarct volume after transient focal cerebral ischemia in rats.* J Cereb Blood Flow Metab, 2004. 24(11): p. 1205-13.
46. Aviles, R. J., B. H. Annex, and R. J. Lederman, *Testing clinical therapeutic angiogenesis using basic fibroblast growth factor (FGF-2).* Br J Pharmacol, 2003. 140(4): p. 637-46.
47. Jeon, O., et al., *Synergistic effect of sustained delivery of basic fibroblast growth factor and bone marrow mononuclear cell transplantation on angiogenesis in mouse ischemic limbs.* Biomaterials, 2006. 27(8): p. 1617-25.
48. Xie, D., et al., *Intracavernosal basic fibroblast growth factor improves vasoreactivity in the hypercholesterolemic rabbit.* J Sex Med, 2006. 3(2): p. 223-32.
49. Suetomi, T., et al., *Effect of basic fibroblast growth factor incorporating gelatin microspheres on erectile function in the diabetic rat.* J Urol, 2005. 173(4): p. 1423-8.
50. Dai, Q., et al., *Systemic basic fibroblast growth factor induces favorable histological changes in the corpus cavernosum of hypercholesterolemic rabbits.* J Urol, 2003. 170(2 Pt 1): p. 664-8.
51. de Tejada, I. S., *Therapeutic strategies for optimizing PDE-5 inhibitor therapy in patients with erectile dysfunction considered difficult or challenging to treat.* Int J Impot Res, 2004. 16 Suppl 1: p. S40-2.
52. Traish, A. and N. Kim, *The physiological role of androgens in penile erection: regulation of corpus cavernosum structure and function.* J Sex Med, 2005. 2(6): p. 759-70.
53. Fraunfelder, F. W., H. D. Pomeranz, and R. A. Egan, *Nonarteritic anterior ischemic optic neuropathy and sildenafil.* Arch Ophthalmol, 2006. 124(5): p. 733-4.
54. Evans, R. W., *Sildenafil can trigger cluster headaches.* Headache, 2006. 46(1): p. 173-4.
55. Schwarz, E. R. and J. Rodriguez, *Sex and the heart.* Int J Impot Res, 2005. 17 Suppl 1: p. S4-6.
56. Rashid, A., *The efficacy and safety of PDE5 inhibitors.* Clin Cornerstone, 2005. 7(1): p. 47-56.
57. Shinlapawittayatorn, K., S. Chattipakorn, and N. Chattipakorn, *Effect of sildenafil citrate on the cardiovascular system.* Braz J Med Biol Res, 2005. 38(9): p. 1303-11.
58. Galie, N., et al., *Sildenafil citrate therapy for pulmonary arterial hypertension.* N Engl J Med, 2005. 353(20): p. 2148-57.
59. Kulkarni, S. K. and C. S. Patil, *Phosphodiesterase 5 enzyme and its inhibitors: update on pharmacological and therapeutical aspects.* Methods Find Exp Clin Pharmacol, 2004. 26(10): p. 789-99.
60. Czp, A., *Citrulline, Viagra and BiDil—bad medicine.* Altern Med Rev, 2005. 10(4): p. 265-7.
61. Golijanin, D., et al., *Doppler evaluation of erectile dysfunction—Part 2.* Int J Inpot Res, 2006.
62. Aversa, A., R. Bruzziches, and G. Spera, *Diagnosing erectile dysfunction: the penile dynamic colour duplex ultrasound revisited.* Int J Androl, 2005. 28 Suppl 2: p. 61-3.
63. Hilson, A. J. and C. A. Lewis, *Radionuclide studies in impotence.* Semin Nucl Med, 1991. 21(2): p. 159-64.
64. Linsenmeyer, T. A., *Evaluation and treatment of erectile dysfunction following spinal cord injury: a review.* J Am Paraplegia Soc, 1991. 14(2): p. 43-51.
65. Higashi, Y., et al., *Oxidative stress, endothelial function and angiogenesis induced by cell therapy and gene therapy.* Curr Pharm Biotechnol, 2006. 7(2): p. 109-16.
66. Tonnesen, M. G., X. Feng, and R. A. Clark, *Angiogenesis in wound healing.* J Investig Dermatol Symp Proc, 2000. 5(1): p. 40-6.
67. Vogel, G., *Cell biology. Ready or not? Human ES cells head toward the clinic.* Science, 2005. 308(5728): p. 1534-8.
68. Shibata, H., et al., *Improved safety of hematopoietic transplantation with monkey embryonic stem cells in the allogeneic setting.* Stem Cells, 2006. 24(6): p. 1450-7.
69. Dufrane, D., et al., *Six-month survival of microencapsulated pig islets and alginate biocompatibility in primates: proof of concept.* Transplantation, 2006. 81(9): p. 1345-53.
70. Jones, K. S., M. V. Sefton, and R. M. Gorczynski, *In vivo recognition by the host adaptive immune system of microencapsulated xenogeneic cells.* Transplantation, 2004. 78(10): p. 1454-62.
71. Mai, G., et al., *Treatment of fulminant liver failure by transplantation of microencapsulated primary or immortalized xenogeneic hepatocytes.* Xenotransplantation, 2005. 12(6): p. 457-64.
72. Rahman, T. M., et al., *Co-transplantation of encapsulated HepG2 and rat Sertoli cells improves outcome in a thioacetamide induced rat model of acute hepatic failure.* Transpl Int, 2005. 18(8): p. 1001-9.
73. Emerich, D. F. and H. C. Salzberg, *Update on immunoisolation cell therapy for CNS diseases.* Cell Transplant, 2001. 10(1): p. 3-24.
74. Levenberg, S., *Engineering blood vessels from stem cells: recent advances and applications.* Curr Opin Biotechnol, 2005. 16(5): p. 516-23.
75. Trounson, A., *The production and directed differentiation of human embryonic stem cells.* Endocr Rev, 2006. 27(2): p. 208-19.
76. Gerecht-Nir, S., et al., *Human embryonic stem cells as an in vitro model for human vascular development and the induction of vascular differentiation.* Lab Invest, 2003. 83(12): p. 1811-20.
77. Peng, H. and G. Chen, *Neural precursors derived from human embryonic stem cells.* Sci China C Life Sci, 2005. 48(3): p. 295-9.
78. Demir, R., et al., *Classification of human placental stem villi: review of structural and functional aspects.* Microsc Res Tech, 1997. 38(1-2): p. 29-41.
79. Portmann-Lanz, C. B., et al., *Placental mesenchymal stem cells as potential autologous graft for pre- and perinatal neuroregeneration.* Am J Obstet Gynecol, 2006. 194(3): p. 664-73.
80. Mohamed, A. A., et al., *Ex vivo expansion of stem cells: defining optimum conditions using various cytokines.* Lab Hematol, 2006. 12(2): p. 86-93.
81. Kashiwakura, I. and T. A. Takahashi, *Fibroblast growth factor and ex vivo expansion of hematopoietic progenitor cells.* Leuk Lymphoma, 2005. 46(3): p. 329-33.
82. Mineishi, S., *[Immunobiology of mini-transplant].* Nippon Rinsho, 2003. 61(9): p. 1489-94.
83. Bossolasco, P., et al., *Molecular and phenotypic characterization of human amniotic fluid cells and their differentiation potential.* Cell Res, 2006. 16(4): p. 329-36.
84. Sartore, S., et al., *Amniotic mesenchymal cells autotransplanted in a porcine model of cardiac ischemia do not differentiate to cardiogenic phenotypes.* Eur J Cardiothorac Surg, 2005. 28(5): p. 677-84.
85. Prusa, A. R., et al., *Neurogenic cells in human amniotic fluid.* Am J Obstet Gynecol, 2004. 191(1): p. 309-14.
86. Tsai, M. S., et al., *Clonal amniotic fluid-derived stem cells express characteristics of both mesenchymal and neural stem cells.* Biol Reprod, 2006. 74(3): p. 545-51.

87. Caplan, A. I. and J. E. Dennis, *Mesenchymal stem cells as trophic mediators*. J Cell Biochem, 2006.
88. Shyu, K. G., et al., *Mesenchymal stem cells are superior to angiogenic growth factor genes for improving myocardial performance in the mouse model of acute myocardial infarction*. J Biomed Sci, 2006. 13(1): p. 47-58.
89. Nagaya, N., et al., *Transplantation of mesenchymal stem cells improves cardiac function in a rat model of dilated cardiomyopathy*. Circulation, 2005. 112(8): p. 1128-35.
90. Knippenberg, M., et al., *Adipose tissue-derived mesenchymal stem cells acquire bone cell-like responsiveness to fluid shear stress on osteogenic stimulation*. Tissue Eng, 2005. 11(11-12): p. 1780-8.
91. Zhang, X., et al., *Mesenchymal progenitor cells derived from chorionic villi of human placenta for cartilage tissue engineering*. Biochem Biophys Res Commun, 2006. 340(3): p. 944-52.
92. Shih, D. T., et al., *Isolation and characterization of neurogenic mesenchymal stem cells in human scalp tissue*. Stem Cells, 2005. 23(7): p. 1012-20.
93. Kadivar, M., et al., *In vitro cardiomyogenic potential of human umbilical vein-derived mesenchymal stem cells*. Biochem Biophys Res Commun, 2006. 340(2): p. 639-47.
94. Kern, S., et al., *Comparative Analysis of Mesenchymal Stem Cells from Bone Marrow, Umbilical Cord Blood or Adipose Tissue*. Stem Cells, 2006.
95. Jansen, J. H., et al., *Interleukin-4. A regulatory protein*. Blut, 1990. 60(5): p. 269-74.
96. Zhou, X., et al., *Boosting interleukin-10 production: therapeutic effects and mechanisms*. Curr Drug Targets Immune Endocr Metabol Disord, 2005. 5(4): p. 465-75.
97. Mentink-Kane, M. M. and T. A. Wynn, *Opposing roles for IL-13 and IL-13 receptor alpha 2 in health and disease*. Immunol Rev, 2004. 202: p. 191-202.
98. Kriegel, M. A., et al., *Transforming growth factor-beta: recent advances on its role in immune tolerance*. Curr Rheumatol Rep, 2006. 8(2): p. 138-44.
99. Fernandez-Botran, R., F. A. Crespo, and X. Sun, *Soluble cytokine receptors in biological therapy*. Expert Opin Biol Ther, 2002. 2(6): p. 585-605.
100. Dayer, J. M., *Evidence for the biological modulation of IL-1 activity: the role of IL-1Ra*. Clin Exp Rheumatol, 2002. 20(5 Suppl 27): p. S14-20.
101. Rouas-Freiss, N., et al., *HLA-G proteins in cancer: do they provide tumor cells with an escape mechanism?* Cancer Res, 2005. 65(22): p. 10139-44.
102. Bohana-Kashtan, O. and C. I. Civin, *Fas ligand as a tool for immunosuppression and generation of immune tolerance*. Stem Cells, 2004. 22(6): p. 908-24.
103. Okazaki, T. and T. Honjo, *The PD-1-PD-L pathway in immunological tolerance*. Trends Immunol, 2006. 27(4): p. 195-201.
104. Longhi, M. P., et al., *Holding T cells in check—a new role for complement regulators?* Trends Immunol, 2006. 27(2): p. 102-8.
105. Wahl, S. M., J. M. Orenstein, and W. Chen, *TGF-beta influences the life and death decisions of T lymphocytes*. Cytokine Growth Factor Rev, 2000. 11(1-2): p. 71-9.
106. Mellor, A. L. and D. H. Munn, *IDO expression by dendritic cells: tolerance and tryptophan catabolism*. Nat Rev Immunol, 2004. 4(10): p. 762-74.
107. Serafini, P., I. Borrello, and V. Bronte, *Myeloid suppressor cells in cancer: recruitment, phenotype, properties, and mechanisms of immune suppression*. Semin Cancer Biol, 2006. 16(1): p. 53-65.
108. Matsumoto, R., et al., *Vascular endothelial growth factor-expressing mesenchymal stem cell transplantation for the treatment of acute myocardial infarction*. Arterioscler Thromb Vasc Biol, 2005. 25(6): p. 1168-73.
109. Klein, S., M. Roghani, and D. B. Rifkin, *Fibroblast growth factors as angiogenesis factors: new insights into their mechanism of action*. Exs, 1997. 79: p. 159-92.
110. Chen, C. H., et al., *Fibroblast growth factor 2: from laboratory evidence to clinical application*. Curr Vasc Pharmacol, 2004. 2(1): p. 33-43.
111. Grines, C., et al., *Angiogenic gene therapy with adenovirus 5 fibroblast growth factor-4 (AdSFGF-4): a new option for the treatment of coronary artery disease*. Am J Cardiol, 2003. 92(9B): p. 24N-31N.
112. Dufourcq, P., et al., *FrzA, a secreted frizzled related protein, induced angiogenic response*. Circulation, 2002. 106(24): p. 3097-103.
113. Morisada, T., et al., *Angiopoietins and angiopoietin-like proteins in angiogenesis*. Endothelium, 2006. 13(2): p. 71-9.
114. Murphy, E., K. Imahashi, and C. Steenbergen, *Bcl-2 regulation of mitochondrial energetics*. Trends Cardiovasc Med, 2005. 15(8): p. 283-90.
115. Harada, H. and S. Grant, *Apoptosis regulators*. Rev Clin Exp Hematol, 2003. 7(2): p. 117-38.
116. Guegan, C., et al., *PTD-XIAP protects against cerebral ischemia by anti-apoptotic and transcriptional regulatory mechanisms*. Neurobiol Dis, 2006. 22(1): p. 177-86.
117. Shabsigh, R., *Testosterone therapy in erectile dysfunction and hypogonadism*. J Sex Med, 2005. 2(6): p. 785-92.
118. Sinha-Hikim, I., et al., *Androgen receptor in human skeletal muscle and cultured muscle satellite cells: upregulation by androgen treatment*. J Clin Endocrinol Metab, 2004. 89(10): p. 5245-55.
119. Bernini, G., et al., *Vascular reactivity in congenital hypogonadal men before and after testosterone replacement therapy*. J Clin Endocrinol Metab, 2006. 91(5): p. 1691-7.
120. Littleton-Kearney, M. and P. D. Hurn, *Testosterone as a modulator of vascular behavior*. Biol Res Nurs, 2004. 5(4): p. 276-85.
121. Montuoro, A., et al., *A technique for isolation of bone marrow cells using hydroxyethyl starch (HES) sedimentation agent*. Haematologica, 1991. 76 Suppl 1: p. 7-9.
122. Rubinstein, P., et al., *Processing and cryopreservation of placental/umbilical cord blood for unrelated bone marrow reconstitution*. Proc Natl Acad Sci USA, 1995. 92(22): p. 10119-22.

What is claimed is:

1. A method of treating erectile dysfunction comprising administration of a therapeutically sufficient amount of testosterone in combination with bone marrow mononuclear cells enriched for expression of CD133;
   wherein said administration is systemic or local administration or both of testosterone and injection of said bone marrow mononuclear cells into the corpus cavernosum in an amount sufficient to cause increased smooth muscle mass and angiogenesis in the penile area.

2. The method of claim 1, wherein said cells comprise committed endothelial progenitor cells that are purified from the bone marrow.

3. The method of claim 1, comprising administration of at least about $1 \times 10^6$ cells.

4. The method of claim 1, comprising administration of between about $1 \times 10^6$ to about $1 \times 10^8$ cells.

5. The method of claim 1, wherein said local administration of testosterone is selected from the group consisting of: topical application of testosterone gel; urethral suppository; and intracavernous injection.

6. A method of treating erectile dysfunction comprising administration of a therapeutically sufficient amount of testosterone in combination with bone marrow mononuclear cells enriched for expression of CD133;

wherein said administration is systemic or local administration or both of testosterone and injection of ex vivo expanded bone marrow mononuclear cells into the corpus cavernosum in an amount sufficient to cause increased smooth muscle mass and angiogenesis in the penile area.

7. The method of claim 6, wherein said cells comprise committed endothelial progenitor cells that are purified from the bone marrow.

8. The method of claim 6, comprising administration of at least about $1 \times 10^6$ cells.

9. The method of claim 6, comprising administration of between about $1 \times 10^6$ to about $1 \times 10^8$ cells.

10. The method of claim 6, wherein said local administration of testosterone is selected from the group consisting of: topical application of testosterone gel; urethral suppository; and intracavernous injection.

* * * * *